(12) United States Patent
Sagi et al.

(10) Patent No.: US 10,040,868 B2
(45) Date of Patent: Aug. 7, 2018

(54) ANTIBODIES TARGETED AGAINST LOXL-2 FOR THE TREATMENT OF COLLAGEN-ASSOCIATED PATHOLOGIES

(71) Applicant: Yeda Research and Development Co. Ltd., Rehovot (IL)

(72) Inventors: Irit Sagi, Rehovot (IL); Moran Grossman, Rehovot (IL); Nir Ben-Chetrit, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 15/328,036

(22) PCT Filed: Jul. 24, 2014

(86) PCT No.: PCT/IL2014/050678
§ 371 (c)(1),
(2) Date: Jan. 22, 2017

(87) PCT Pub. No.: WO2016/012993
PCT Pub. Date: Jan. 28, 2016

(65) Prior Publication Data
US 2017/0210823 A1    Jul. 27, 2017

(51) Int. Cl.
| | |
|---|---|
| *A61K 39/00* | (2006.01) |
| *A61K 39/395* | (2006.01) |
| *C07K 16/40* | (2006.01) |
| *A61K 45/06* | (2006.01) |
| *A61K 33/24* | (2006.01) |

(52) U.S. Cl.
CPC ............ *C07K 16/40* (2013.01); *A61K 33/24* (2013.01); *A61K 39/3955* (2013.01); *A61K 45/06* (2013.01); *A61K 2039/505* (2013.01); *A61K 2039/507* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 8,168,180 | B2 | 5/2012 | Neufeld et al. | |
| 8,679,485 | B2 * | 3/2014 | Smith | C07K 16/40 424/130.1 |
| 8,680,246 | B2 * | 3/2014 | McCauley | C07K 16/40 435/810 |
| 2011/0200606 | A1 * | 8/2011 | McCauley | C07K 16/40 424/139.1 |

FOREIGN PATENT DOCUMENTS

| | | |
|---|---|---|
| EP | 2537529 | 12/2012 |
| WO | WO 2012/139045 | 10/2012 |
| WO | WO 2016/012993 | 1/2016 |

OTHER PUBLICATIONS

Ahn et al. 2013. Breast Cancer Res Treat. 141:89-99.*
International Search Report and the Written Opinion dated Oct. 21, 2014 From the International Searching Authority Re. Application No. PCT/IL2014/050678.
Barker et al. "Tumor-Secreted LOXL2 Activates Fibroblasts Through FAK Signaling", Molecular Cancer Research, 11: 1425-1436, Published Online Sep. 5, 2013.
Barry-Hamilton et al. "Allosteric Inhibition of Lysyl Oxidase-Like-2 Impedes the Development of a Pathologic Microenvironment", Nature Medicine, 16(9): 1009-1017, Sep. 5, 2010.
Grossman "Controlling the Extracellular Function of Lysyl Oxidase Like Protein 2 by Monoclonal Antibodies Has Therapeutic Potentail on Cell Invasion and Angiogenesis", Poster Presentation, Presented at ILANIT 2014, Israel, 15 P., 2014.
Mammoto et al. "Control of Lung Vascular Permeability and Endotoxin-Induced Pulmonary Oedema by Chenges in Extracellular Matrix Mechanics", Nature Communciations, 4(Art.1759): 1-5, Apr. 23, 2013. Abstract.
International Preliminary Report on Patentability dated Feb. 2, 2017 From the International Bureau of WIPO Re. Application No. PCT/IL2014/050678. (10 Pages).

* cited by examiner

*Primary Examiner* — Shulamith H Shafer

(57) ABSTRACT

An article of manufacture is disclosed which comprises at least two active agents, wherein a first of the two active agents comprises an anti-cancer agent or an antifibrotic agent and a second of the at least two active agents down-regulates the activity and/or expression of lysyl-oxidase like protein-2 (LOXL-2) and which is capable of altering the structure of the extracellular matrix.

11 Claims, 14 Drawing Sheets
(11 of 14 Drawing Sheet(s) Filed in Color)

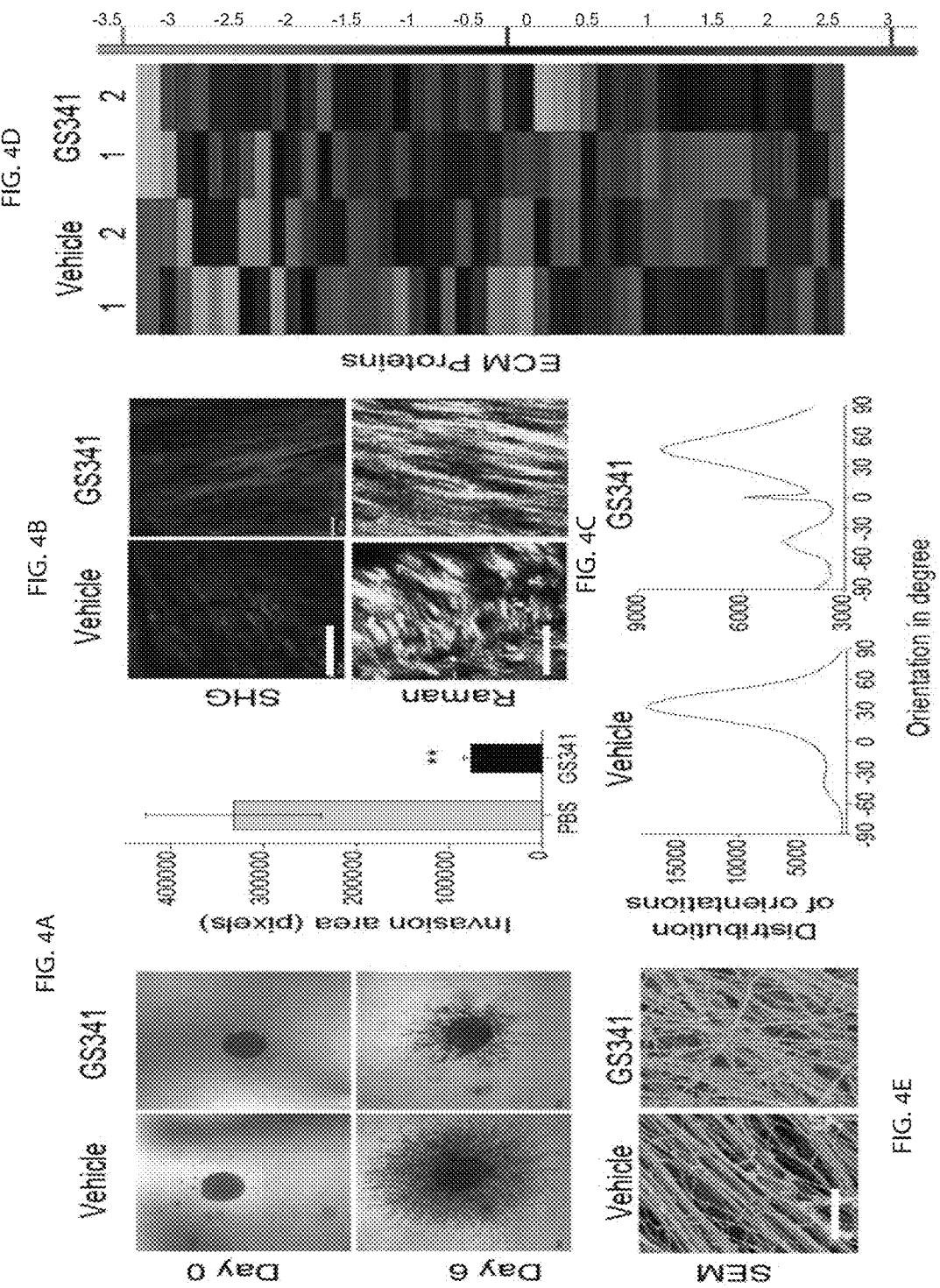

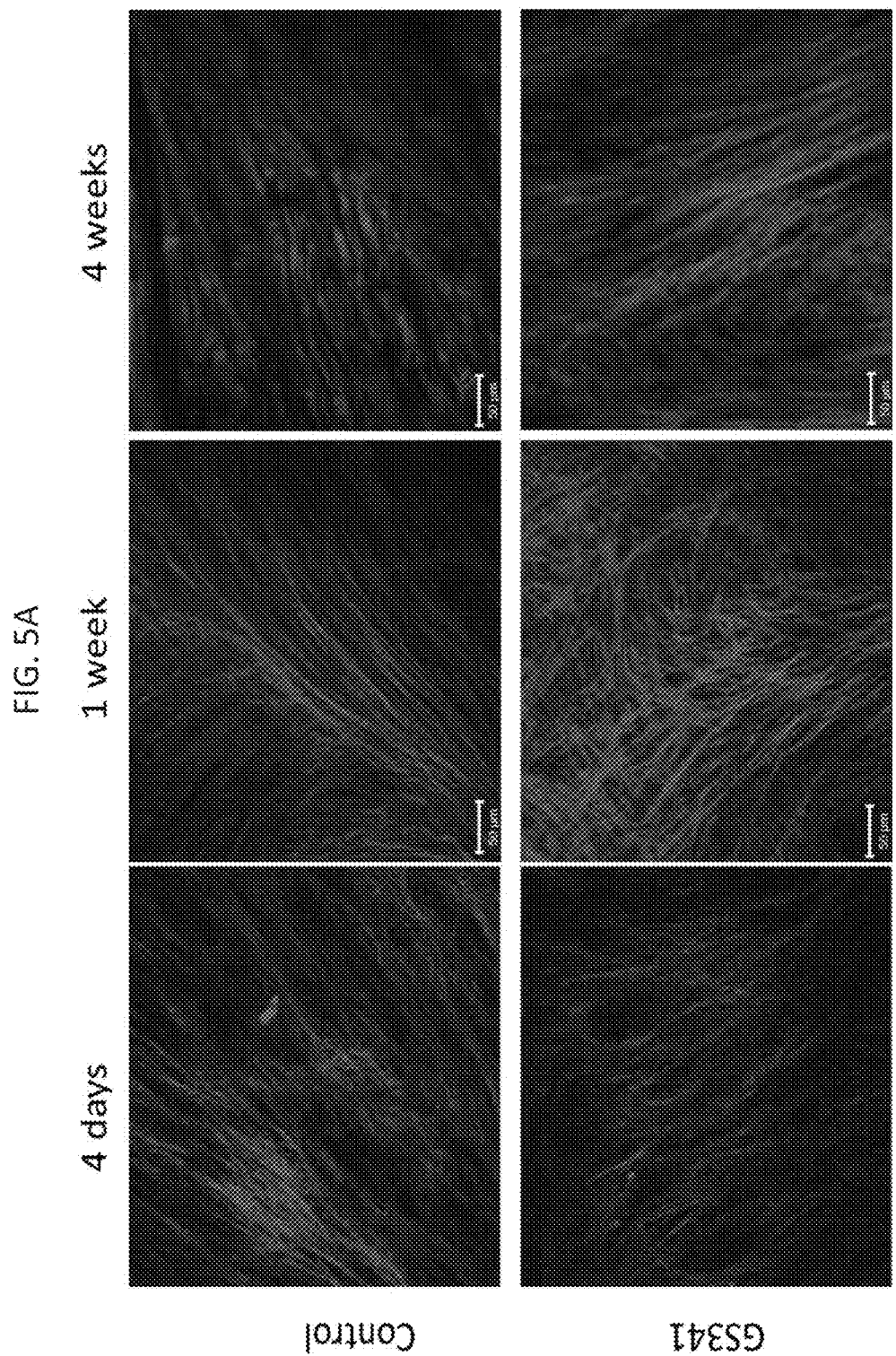

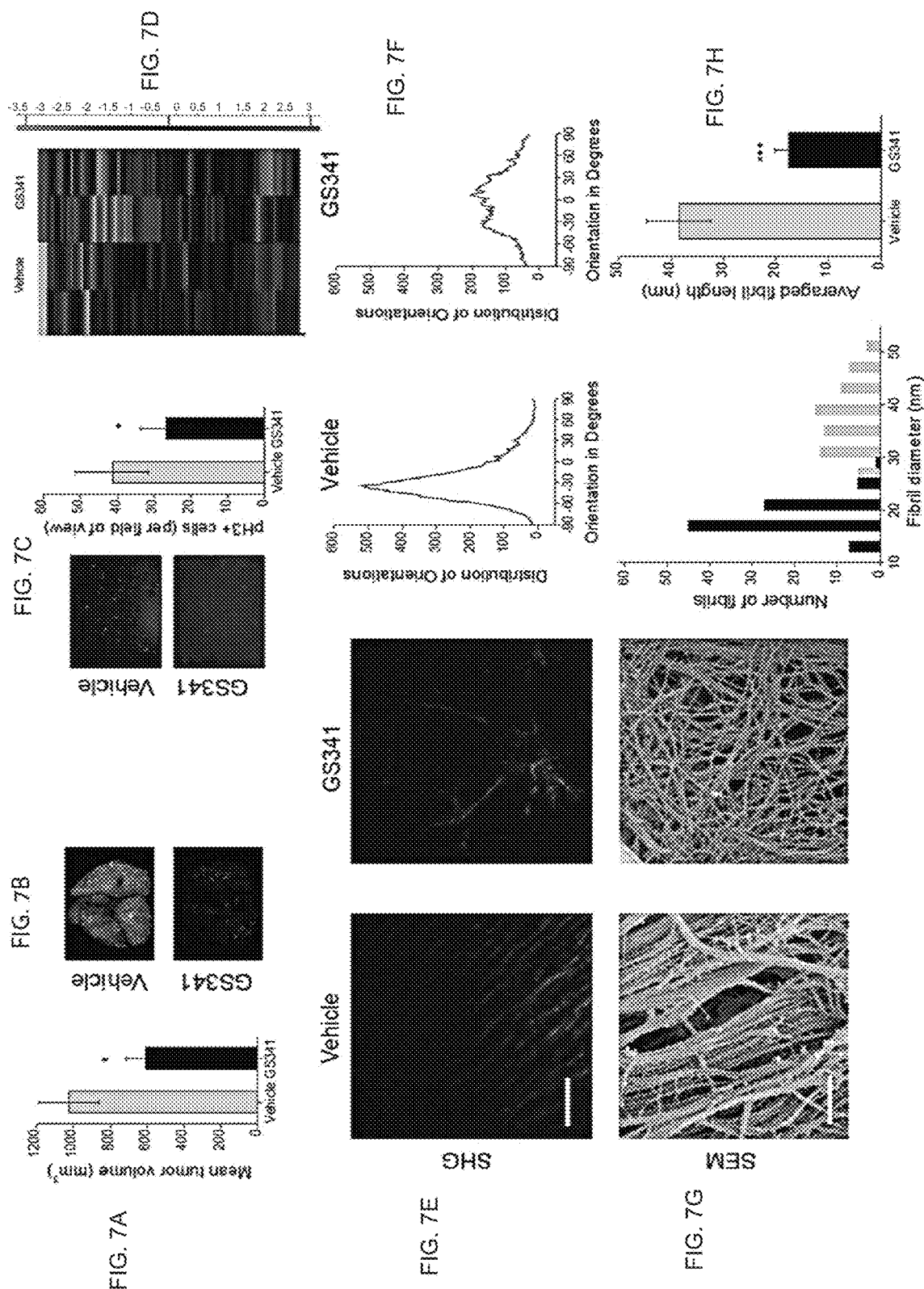

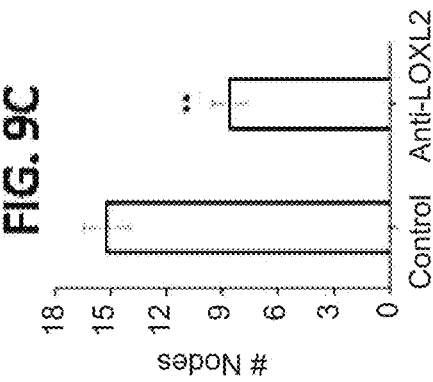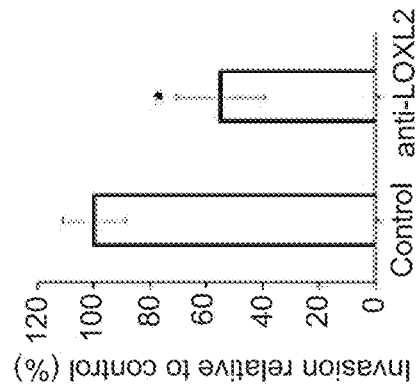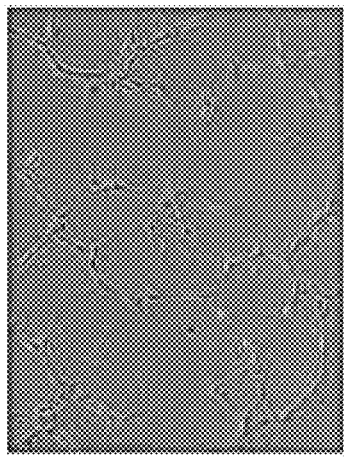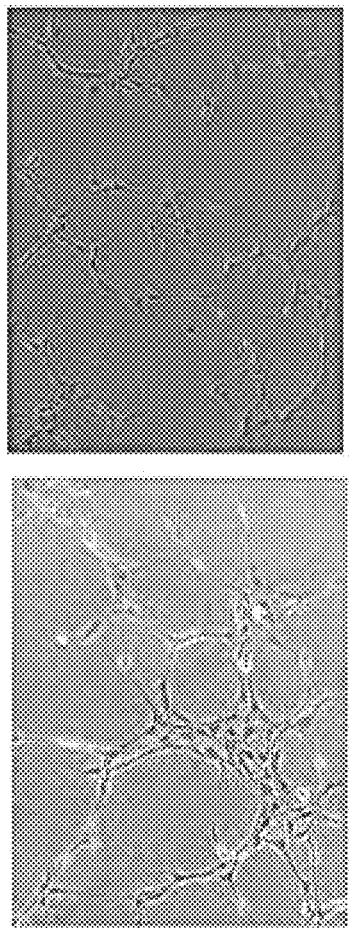

1μM anti-LOXL2 + anti-MMP-9

1μM Control IgG

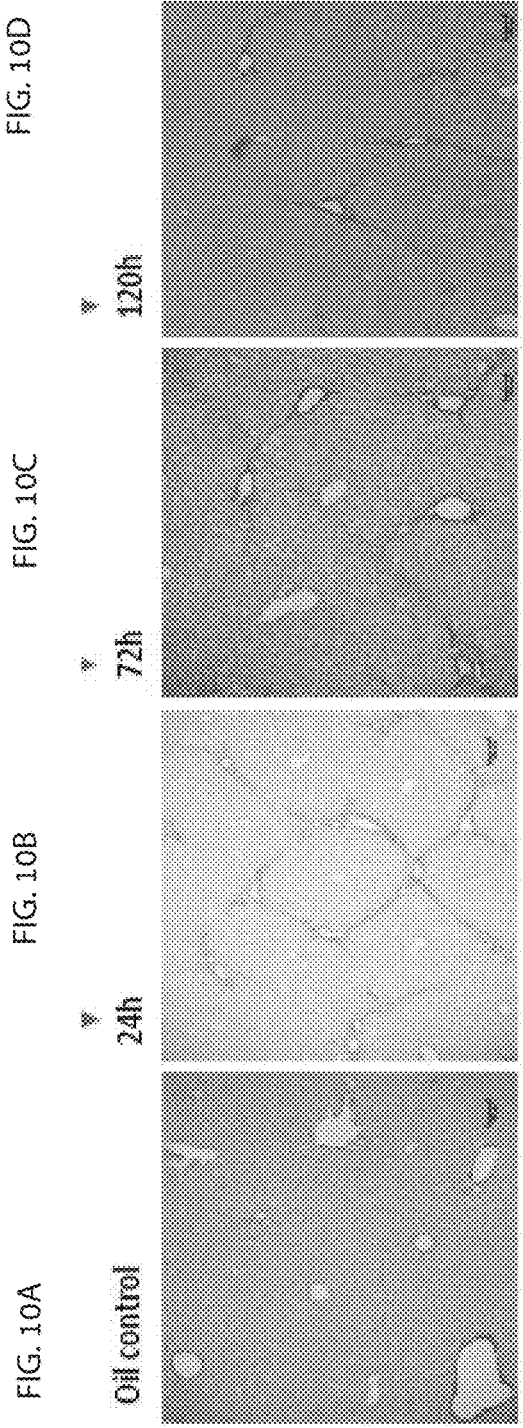
FIG. 10A Oil control
FIG. 10B 24h
FIG. 10C 72h
FIG. 10D 120h
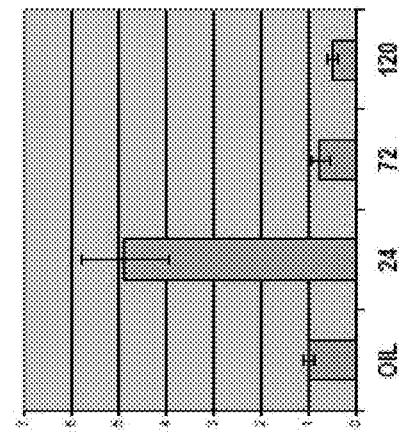
FIG. 10E Fab GS341

PBS amount of collgen

SEQUENCE LISTING

```
<160> NUMBER OF SEQ ID NOS: 10

<210> SEQ ID NO 1
<211> LENGTH: 119
<212> TYPE: PRT
<213> ORGANISM: Homo sapiens

<400> SEQUENCE: 1

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Asn Tyr
            20                  25                  30

Trp Met Ser Trp Val Lys Gln Arg Pro Gly Gln Gly Leu Glu Trp Ile
        35                  40                  45

Gly Met Ile His Pro Ser Asp Thr Asp Ile Arg Leu His Gln Lys Phe
    50                  55                  60

Lys Asp Lys Ala Thr Leu Thr Val Asp Lys Ser Ser Ser Thr Ala Tyr
65                  70                  75                  80

Val Gln Leu Ser Ser Pro Thr Ser Glu Asp Ser Ala Val Tyr Tyr Cys
```

```
                85                  90                  95

Ala Arg Gly Gly Gln Leu Gly Pro Trp Phe Ala Tyr Trp Gly Gln Gly
            100                 105                 110

Thr Leu Val Thr Val Ser Ala
        115

<210> SEQ ID NO 2
<211> LENGTH: 111
<212> TYPE: PRT
<213> ORGANISM: Homo sapiens

<400> SEQUENCE: 2

Asp Ile Val Met Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Phe Thr Leu Asn Ile His Pro
65                  70                  75                  80

Val Glu Glu Glu Asp Ala Ala Thr Tyr Tyr Cys Gln His Ser Arg Glu
                85                  90                  95

Leu Pro Trp Thr Phe Gly Gly Gly Thr Lys Leu Glu Ile Lys Arg
            100                 105                 110

<210> SEQ ID NO 3
<211> LENGTH: 8
<212> TYPE: PRT
<213> ORGANISM: Homo sapiens

<400> SEQUENCE: 3

Gly Tyr Ser Phe Thr Asn Tyr Trp
1               5

<210> SEQ ID NO 4
<211> LENGTH: 8
<212> TYPE: PRT
<213> ORGANISM: Homo sapiens

<400> SEQUENCE: 4

Ile His Pro Ser Asp Thr Asp Ile
1               5

<210> SEQ ID NO 5
<211> LENGTH: 12
<212> TYPE: PRT
<213> ORGANISM: Homo sapiens

<400> SEQUENCE: 5

Ala Arg Gly Gly Gln Leu Gly Pro Trp Phe Ala Tyr
1               5                   10

<210> SEQ ID NO 6
<211> LENGTH: 11
<212> TYPE: PRT
<213> ORGANISM: Homo sapiens

<400> SEQUENCE: 6

Ser Lys Ser Val Ser Thr Ser Gly Tyr Ser Tyr
```

<210> SEQ ID NO 7
<211> LENGTH: 3
<212> TYPE: PRT
<213> ORGANISM: Homo sapiens

<400> SEQUENCE: 7

Leu Ala Ser
1

<210> SEQ ID NO 8
<211> LENGTH: 9
<212> TYPE: PRT
<213> ORGANISM: Homo sapiens

<400> SEQUENCE: 8

Gln His Ser Arg Glu Leu Pro Trp Thr
1               5

<210> SEQ ID NO 9
<211> LENGTH: 774
<212> TYPE: PRT
<213> ORGANISM: Homo sapiens

<400> SEQUENCE: 9

Met Glu Arg Pro Leu Cys Ser His Leu Cys Ser Cys Leu Ala Met Leu
1               5                   10                  15

Ala Leu Leu Ser Pro Leu Ser Leu Ala Gln Tyr Asp Ser Trp Pro His
                20                  25                  30

Tyr Pro Glu Tyr Phe Gln Gln Pro Ala Pro Glu Tyr His Gln Pro Gln
            35                  40                  45

Ala Pro Ala Asn Val Ala Lys Ile Gln Leu Arg Leu Ala Gly Gln Lys
        50                  55                  60

Arg Lys His Ser Glu Gly Arg Val Glu Val Tyr Tyr Asp Gly Gln Trp
65                  70                  75                  80

Gly Thr Val Cys Asp Asp Asp Phe Ser Ile His Ala Ala His Val Val
                85                  90                  95

Cys Arg Glu Leu Gly Tyr Val Glu Ala Lys Ser Trp Thr Ala Ser Ser
            100                 105                 110

Ser Tyr Gly Lys Gly Glu Gly Pro Ile Trp Leu Asp Asn Leu His Cys
        115                 120                 125

Thr Gly Asn Glu Ala Thr Leu Ala Ala Cys Thr Ser Asn Gly Trp Gly
130                 135                 140

Val Thr Asp Cys Lys His Thr Glu Asp Val Gly Val Val Cys Ser Asp
145                 150                 155                 160

Lys Arg Ile Pro Gly Phe Lys Phe Asp Asn Ser Leu Ile Asn Gln Ile
                165                 170                 175

Glu Asn Leu Asn Ile Gln Val Asp Ile Arg Ile Arg Ala Ile Leu
            180                 185                 190

Ser Thr Tyr Arg Lys Arg Thr Pro Val Met Glu Gly Tyr Val Glu Val
        195                 200                 205

Lys Glu Gly Lys Thr Trp Lys Gln Ile Cys Asp Lys His Trp Thr Ala
210                 215                 220

Lys Asn Ser Arg Val Val Cys Gly Met Phe Gly Phe Pro Gly Glu Arg
225                 230                 235                 240

Thr Tyr Asn Thr Lys Val Tyr Lys Met Phe Ala Ser Arg Arg Lys Gln
                245                 250                 255

```
Arg Tyr Trp Pro Phe Ser Met Asp Cys Thr Gly Thr Glu Ala His Ile
            260                 265                 270

Ser Ser Cys Lys Leu Gly Pro Gln Val Ser Leu Asp Pro Met Lys Asn
        275                 280                 285

Val Thr Cys Glu Asn Gly Leu Pro Ala Val Val Ser Cys Val Pro Gly
    290                 295                 300

Gln Val Phe Ser Pro Asp Gly Pro Ser Arg Phe Arg Lys Ala Tyr Lys
305                 310                 315                 320

Pro Glu Gln Pro Leu Val Arg Leu Arg Gly Ala Tyr Ile Gly Glu
                325                 330                 335

Gly Arg Val Glu Val Leu Lys Asn Gly Glu Trp Gly Thr Val Cys Asp
            340                 345                 350

Asp Lys Trp Asp Leu Val Ser Ala Ser Val Val Cys Arg Glu Leu Gly
        355                 360                 365

Phe Gly Ser Ala Lys Glu Ala Val Thr Gly Ser Arg Leu Gly Gln Gly
    370                 375                 380

Ile Gly Pro Ile His Leu Asn Glu Ile Gln Cys Thr Gly Asn Glu Lys
385                 390                 395                 400

Ser Ile Ile Asp Cys Lys Phe Asn Ala Glu Ser Gln Gly Cys Asn His
                405                 410                 415

Glu Glu Asp Ala Gly Val Arg Cys Asn Thr Pro Ala Met Gly Leu Gln
            420                 425                 430

Lys Lys Leu Arg Leu Asn Gly Gly Arg Asn Pro Tyr Glu Gly Arg Val
        435                 440                 445

Glu Val Leu Val Glu Arg Asn Gly Ser Leu Val Trp Gly Met Val Cys
    450                 455                 460

Gly Gln Asn Trp Gly Ile Val Glu Ala Met Val Val Cys Arg Gln Leu
465                 470                 475                 480

Gly Leu Gly Phe Ala Ser Asn Ala Phe Gln Glu Thr Trp Tyr Trp His
                485                 490                 495

Gly Asp Val Asn Ser Asn Lys Val Val Met Ser Gly Val Lys Cys Ser
            500                 505                 510

Gly Thr Glu Leu Ser Leu Ala His Cys Arg His Asp Gly Glu Asp Val
        515                 520                 525

Ala Cys Pro Gln Gly Gly Val Gln Tyr Gly Ala Gly Val Ala Cys Ser
    530                 535                 540

Glu Thr Ala Pro Asp Leu Val Leu Asn Ala Glu Met Val Gln Gln Thr
545                 550                 555                 560

Thr Tyr Leu Glu Asp Arg Pro Met Phe Leu Gln Cys Ala Met Glu
                565                 570                 575

Glu Asn Cys Leu Ser Ala Ser Ala Ala Gln Thr Asp Pro Thr Thr Gly
            580                 585                 590

Tyr Arg Arg Leu Leu Arg Phe Ser Ser Gln Ile His Asn Asn Gly Gln
        595                 600                 605

Ser Asp Phe Arg Pro Lys Asn Gly Arg His Ala Trp Ile Trp His Asp
    610                 615                 620

Cys His Arg His Tyr His Ser Met Glu Val Phe Thr His Tyr Asp Leu
625                 630                 635                 640

Leu Asn Leu Asn Gly Thr Lys Val Ala Glu Gly His Lys Ala Ser Phe
                645                 650                 655

Cys Leu Glu Asp Thr Glu Cys Glu Gly Asp Ile Gln Lys Asn Tyr Glu
            660                 665                 670
```

| | | | | | | | | | | |
|---|---|---|---|---|---|---|---|---|---|---|
|Cys|Ala|Asn|Phe|Gly|Asp|Gln|Gly|Ile|Thr|Met|Gly|Cys|Trp|Asp|Met|
| | | |675| | | |680| | | |685| | | | |

Tyr Arg His Asp Ile Asp Cys Gln Trp Val Asp Ile Thr Asp Val Pro
        690             695                 700

Pro Gly Asp Tyr Leu Phe Gln Val Val Ile Asn Pro Asn Phe Glu Val
705             710                 715                 720

Ala Glu Ser Asp Tyr Ser Asn Asn Ile Met Lys Cys Arg Ser Arg Tyr
            725                 730                 735

Asp Gly His Arg Ile Trp Met Tyr Asn Cys His Ile Gly Gly Ser Phe
                740                 745                 750

Ser Glu Glu Thr Glu Lys Lys Phe Glu His Phe Ser Gly Leu Leu Asn
        755                 760                 765

Asn Gln Leu Ser Pro Gln
    770

<210> SEQ ID NO 10
<211> LENGTH: 2325
<212> TYPE: DNA
<213> ORGANISM: Homo sapiens

<400> SEQUENCE: 10

```
atggagaggc ctctgtgctc ccacctctgc agctgcctgg ctatgctggc cctcctgtcc      60
cccctgagcc tggcacagta tgacagctgg ccccattacc ccgagtactt ccagcaaccg     120
gctcctgagt atcaccagcc ccaggccccc gccaacgtgg ccaagattca gctgcgcctg    180
gctgggcaga gaggaagca cagcgagggc cgggtggagg tgtactatga tggccagtgg     240
ggcaccgtgt gcgatgacga cttctccatc cacgctgccc acgtcgtctg ccgggagctg    300
ggctacgtgg aggccaagtc ctggactgcc agctcctcct acggcaaggg agaagggccc    360
atctggttag acaatctcca ctgtactggc aacgaggcga cccttgcagc atgcacctcc    420
aatggctggg gcgtcactga ctgcaagcac acggaggatg tcggtgtggt gtgcagcgac    480
aaaaggattc ctgggttcaa atttgacaat tcgttgatca accagataga gaacctgaat    540
atccaggtgg aggacattcg gattcgagcc atcctctcaa cctaccgcaa gcgcacccca    600
gtgatggagg gctacgtgga ggtgaaggag ggcaagacct ggaagcagat ctgtgacaag    660
cactggacgg ccaagaattc ccgcgtggtc tgcggcatgt ttggcttccc tggggagagg    720
acatacaata ccaaagtgta caaatgtttt gcctcacgga ggaagcagcg ctactggcca    780
ttctccatgg actgcaccgg cacagaggcc cacatctcca gctgcaagct gggcccccag    840
gtgtcactgg accccatgaa gaatgtcacc tgcgagaatg gctaccggc cgtggtgagt    900
tgtgtgcctg gcaggtcctt cagccctgac ggaccctcaa gattccggaa agcgtacaag    960
ccagagcaac ccctggtgcg actgagaggc ggtgcctaca tcggggaggg ccgcgtggag   1020
gtgctcaaaa atggagaatg ggggaccgtc tgcgacgaca gtgggacct ggtgtcggcc    1080
agtgtggtct gcagagagct gggctttggg agtgccaaag aggcagtcac tggctcccga    1140
ctggggcaag ggatcggacc catccacctc aacgagatcc agtgcacagg caatgagaag    1200
tccattatag actgcaagtt caatgccgag tctcagggct gcaaccacga ggaggatgct    1260
ggtgtgagat gcaacacccc tgccatgggc ttgcagaaga gctgcgcct gaacggcggc    1320
cgcaatccct acgagggccg agtggaggtg ctggtggaga aaacgggtc ccttgtgtgg   1380
gggatggtgt gtggccaaaa ctggggcatc gtggaggcca tggtggtctg ccgccagctg    1440
ggcctgggat cgccagcaa cgccttccag gagacctggt attggcacgg agatgtcaac    1500
```

```
agcaacaaag tggtcatgag tggagtgaag tgctcgggaa cggagctgtc cctggcgcac  1560
tgccgccacg acggggagga cgtggcctgc ccccagggcg gagtgcagta cggggccgga  1620
gttgcctgct cagaaaccgc ccctgacctg gtcctcaatg cggagatggt gcagcagacc  1680
acctacctgg aggaccggcc catgttcatg ctgcagtgtg ccatggagga gaactgcctc  1740
tcggcctcag ccgcgcagac cgaccccacc acgggctacc gccggctcct gcgcttctcc  1800
tcccagatcc acaacaatgg ccagtccgac ttccggccca agaacggccg ccacgcgtgg  1860
atctggcacg actgtcacag gcactaccac agcatggagg tgttcaccca ctatgacctg  1920
ctgaacctca atggcaccaa ggtggcagag ggccacaagg ccagcttctg cttggaggac  1980
acagaatgtg aaggagacat ccagaagaat tacgagtgtg ccaacttcgg cgatcagggc  2040
atcaccatgg gctgctggga catgtaccgc catgacatcg actgccagtg ggttgacatc  2100
actgacgtgc cccctggaga ctacctgttc caggttgtta ttaacccccaa cttcgaggtt  2160 gcagaatccg attactccaa caacatcatg aaatgcagga gccgctatga cggccaccgc  2220
atctggatgt acaactgcca cataggtggt tccttcagcg aagagacgga aaaaaagttt  2280
gagcacttca gcgggctctt aaacaaccag ctgtccccgc agtaa              2325
```

ANTIBODIES TARGETED AGAINST LOXL-2 FOR THE TREATMENT OF COLLAGEN-ASSOCIATED PATHOLOGIES

RELATED APPLICATIONS

This application is a National Phase of PCT Patent Application No. PCT/IL2014/050678 having International filing date of Jul. 24, 2014, the contents of which are incorporated by reference as if fully set forth herein in their entirety.

SEQUENCE LISTING STATEMENT

The ASCII file, entitled 68315SequenceListing.txt, created on Jan. 22, 2017, comprising 13,060 bytes, submitted concurrently with the filing of this application is incorporated herein by reference.

FIELD AND BACKGROUND OF THE INVENTION

The present invention, in some embodiments thereof, relates to antibodies targeted against lysyl-oxidase like protein-2 (LOXL-2) which are capable of altering the architecture of pathologocial collagen assembly.

The extracellular matrix (ECM) is an essential mediator of tissue function that provides both chemical and mechanical stimuli to influence cellular behavior in both health and disease. The ECM consists of a mesh of fibrillar and non-fibrillar collagens, elastic fibers, glycoproteins and proteoglycans that assemble into complex networks in a tissue specific manner which determine the biophysical properties of tissues such as stiffness, compliance and resilience. Remodeling of the ECM by a variety of tissue remodeling enzymes that cross-link, glycosylate and/or degrade the ECM, can create space for cells to migrate, regulate tissue architecture, and activate, deactivate, or alter the activity of signaling molecules. Tightly controlled ECM homeostasis is therefore essential for life, and dysregulated ECM remodeling can result with pathologic outcomes such as cancer and fibrosis. Indeed, over-expression of tissue remodeling enzymes is one of the hallmarks of cancer and examination of ECM derived from solid tumors reveals massive deposition of collagen, altered ECM morphology and increased tissue stiffness. In addition, proteomic analyses have demonstrated that the composition of the tumor extracellular matrix changes with tumor metastatic potential. Thus, controlling ECM morphology and composition is considered as potent therapeutic strategy for cancer patients (Siddikuzzaman, Grace, V. M. & Guruvayoorappan, C. Inflammopharmacology 19, 117-29 (2011). However, despite the growing amount of data correlating between ECM biophysical properties and tumor malignancy, how to clinically interfere with the altered biophysical ECM during the onset and progression of cancer is unknown.

The lysyl oxidases (LOX) comprise a family of five copper-dependent amine oxidases homologs enzymes (LOX and LOXL1-4) that initiate the process of covalent intra- and intermolecular cross-linking of collagens and elastin. Among the LOX family, LOX and LOXL2 are highly expressed in many human cancers, partly and adversely in correlation to clinical outcome. Activation of LOX family members during cancer has been demonstrated to increase the stiffness of the tissue due to extensive crosslinking of collagen fibrils and to effect downstream signals by modification of snail and integrins, repression of E-cadherin leading to induction of epithelial to mesenchymal (EMT) transition. Interestingly, LOXL2 is highly over-expressed mainly in invasive metastatic tumors more than noninvasive tumors, and is linked to promoting tumor cell invasion, angiogenesis and remodeling of the tumor microenvironment. LOXL2 has been proposed to function both extracellularly and intracellularly to activate oncogenic signaling pathways leading to epithelial-mesenchymal transition (EMT) by and invasion of breast cancer cells. In the tumor stroma, LOXL2 mediates fibroblast activation through integrin engagement and FAK signaling. It has been recently shown that LOXL2 and the transcription factor, E47, contribute to early steps of metastatic colonization by cell and noncell autonomous functions regulating the recruitment of bone marrow progenitor cells to the lungs and by direct transcriptional regulation of fibronectin and cytokines TNFα, ANG-1 and GM-CSF. Genetic, chemical or antibody inhibition of LOXL2 significantly reduced lungs, liver and bone metastasis through its effect on matrix remodeling and cell invasion (Barker, H. E. et al. Cancer Res 71, 1561-72 (2011); Barry-Hamilton, V. et al. Nat Med 16, 1009-17 (2010)).

An antibody developed to specifically target the fourth SRCR domain of LOXL-2 is disclosed in Barry-Hamilton V. et al., Nat Med. 2010 September; 16(9):1009-17.

An antibody targeted to the catalytic site of LOXL-2 is disclosed in U.S. Pat. No. 8,168,180.

SUMMARY OF THE INVENTION

According to an aspect of some embodiments of the present invention there is provided an article of manufacture comprising at least two active agents, wherein a first of the two active agents comprises an anti-cancer agent or an antifibrotic agent and second of the at least two active agents downregulates the activity and/or expression of lysyl-oxidase like protein-2 (LOXL-2) and which is capable of altering the structure of the extracellular matrix.

According to an aspect of some embodiments of the present invention there is provided an isolated antibody comprising an antigen recognition region which specifically binds to lysyl-oxidase like protein-2 (LOXL-2) and being capable of down-regulating crosslinking of type I collagen in vitro.

According to an aspect of some embodiments of the present invention there is provided an isolated antibody comprising an antigen recognition region which comprises CDR amino acid sequences as set forth in SEQ ID NOs: 3, 4, 5, 6, 7 and 8.

According to an aspect of some embodiments of the present invention there is provided a method of treating a disease associated with aberrant collagen deposition in a subject in need thereof, comprising administering to the subject a therapeutically effective amount of the antibody disclosed herein, thereby treating the disease.

According to an aspect of some embodiments of the present invention there is provided an article of manufacture comprising an isolated antibody comprising an antigen recognition region which comprises CDR amino acid sequences set forth in SEQ ID NO: 3, 4, 5, 6, 7 and 8 and an anti-cancer agent or an antifibrotic agent.

According to an aspect of some embodiments of the present invention there is provided a method of treating a disease associated with aberrant collagen deposition in a subject in need thereof, comprising administering to the subject a therapeutically effective amount of an agent which downregulates the activity and/or expression of the LOXL-2 and an additional agent selected from the group consisting of an anti-cancer agent and an antifibrotic agent, thereby treating the disease.

According to an aspect of some embodiments of the present invention there is provided a combination of an agent which downregulates the activity and/or expression of the LOXL-2 and an additional agent selected from the group consisting of an anti-cancer agent and an antifibrotic agent for use in treating a disease associated with aberrant collagen deposition.

According to an aspect of some embodiments of the present invention there is provided a pharmaceutical composition comprising the antibody described herein and a pharmaceutically acceptable carrier.

According to an aspect of some embodiments of the present invention there is provided a pharmaceutical composition comprising an anti-cancer agent or an antifibrotic agent as a first active agent and an agent which downregulates the activity and/or expression of lysyl-oxidase like protein-2 (LOXL-2) and which is capable of altering the structure of the extracellular matrix as a second active agent, and a pharmaceutically acceptable carrier.

According to an aspect of some embodiments of the present invention there is provided a bispecific antibody comprising a first antigen-binding domain that specifically binds to LOXL-2 and a second antigen-binding domain that specifically binds to an epitope of a protein that is associated with cancer.

According to some embodiments of the invention, the second agent is an antibody which comprises an antigen recognition region which specifically binds to the LOXL-2.

According to some embodiments of the invention, the antibody specifically binds the catalytic site of the LOXL-2.

According to some embodiments of the invention, the antibody does not bind to the fourth scavenger receptor-cysteine-rich (SRCR) domain of the LOXL-2.

According to some embodiments of the invention, the second agent is a polynucleotide agent which downregulates the expression of the LOXL-2.

According to some embodiments of the invention, the first agent and the second agent are packaged in separate packaging.

According to some embodiments of the invention, the first agent and the second agent are formulated in a single pharmaceutical composition.

According to some embodiments of the invention, the second agent is capable of down-regulating crosslinking of type I collagen in vitro.

According to some embodiments of the invention, the antibody is capable of specifically binding to the catalytic site of the LOXL-2.

According to some embodiments of the invention, the antibody does not bind to the fourth scavenger receptor-cysteine-rich (SRCR) domain of the LOXL-2.

According to some embodiments of the invention, the antibody is for use in treating a disease associated with aberrant collagen deposition.

According to some embodiments of the invention, the agent which downregulates the activity and/or expression of the LOXL-2 does not affect angiogenesis in vivo.

According to some embodiments of the invention, the antigen recognition region comprises CDR amino acid sequences as set forth in SEQ ID NOs: 3, 4, 5, 6, 7 and 8.

According to some embodiments of the invention, the amino acid sequence of the $V_H$ of the antibody is as set forth in SEQ ID NO: 1.

According to some embodiments of the invention, the amino acid sequence of the $V_L$ of the antibody is as set forth in SEQ ID NO: 2.

According to some embodiments of the invention, the anti-cancer agent comprises a chemotherapeutic agent.

According to some embodiments of the invention, the chemotherapeutic agent is cisplatin.

According to some embodiments of the invention, the anti-cancer agent is an antibody.

According to some embodiments of the invention, the antibody binds specifically to MMP-9.

According to some embodiments of the invention, the disease is cancer.

According to some embodiments of the invention, the disease is pulmonary alveolar proteinosis (PAP).

According to some embodiments of the invention, the cancer is breast cancer.

According to some embodiments of the invention, the cancer is colon cancer.

According to some embodiments of the invention, the breast cancer is triple negative breast cancer.

According to some embodiments of the invention, the cancer has metastasized.

According to some embodiments of the invention, the administering of the anti-cancer agent or antifibrotic agent is effected following administering of the agent which downregulates the activity and/or expression of the LOXL-2.

According to some embodiments of the invention, the disease is a fibrotic disease.

According to some embodiments of the invention, the agent which downregulates the activity and/or expression of the LOXL-2 is an antibody which comprises an antigen recognition region which specifically binds to the LOXL-2, the antibody being capable of down-regulating crosslinking of type I collagen in vitro.

According to some embodiments of the invention, the agent which downregulates the activity and/or expression of the LOXL-2 does not affect angiogenesis in vivo.

According to some embodiments of the invention, the antigen recognition region comprises CDR amino acid sequences as set forth in SEQ ID NO: 3, 4, 5, 6, 7 and 8.

According to some embodiments of the invention, the amino acid sequence of the $V_H$ of the antibody is as set forth in SEQ ID NO: 1.

According to some embodiments of the invention, the amino acid sequence of the $V_L$ of the antibody is as set forth in SEQ ID NO: 2.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
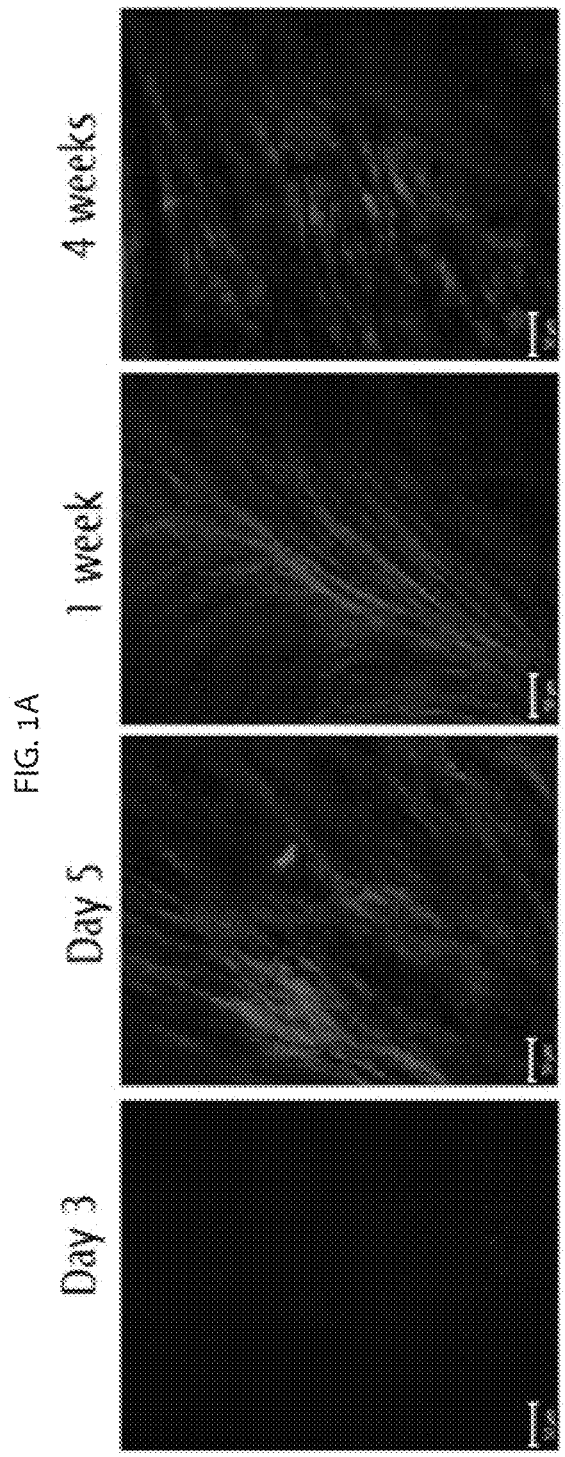
Figure 1C:
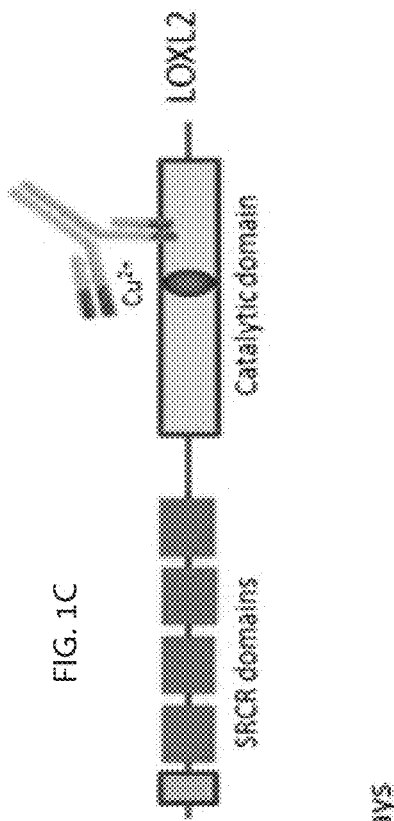
Figure 1B:
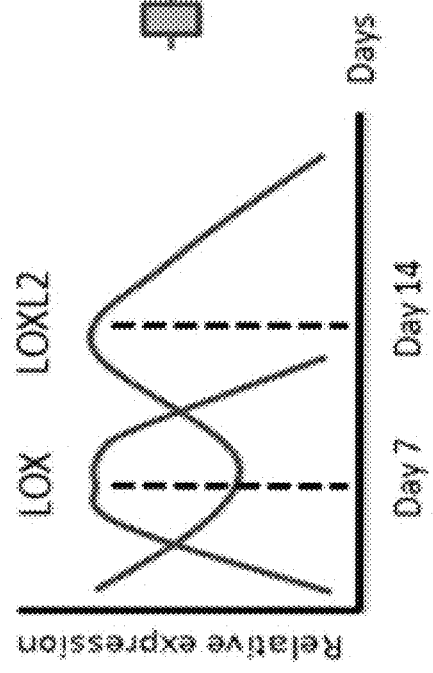

FIGS. 1A-C Characterization of ECM maturation by human dermal fibroblasts. A) representative two-photon SHG images of collagen at various time points, depicting collagen synthesis (day 5), assembly into linear fibrils (day 7) and maturation into cross-linked collagen fibers (4 weeks). Scale bar 50 μm. B) LOXL2 therapeutic window. A scheme illustrating over-expression of LOXL2 at later stages of collagen assembly based on qPCR analysis of representative collagen crosslinking enzymes (Lox and Lox12), and major collagens found in basement membrane (Col I and Col IV) (see FIGS. 2A-D for qPCR full analysis). C) Domain organization of LOXL2: pre domain (pink), four SRCR domains (blue), and Cu2+-dependent catalytic domain (residues 545-775). This domain was cloned into recombinant expression system, and used for immunizing mice in order to develop specific antibodies against the catalytic activity of LOXL2.

Figure 2A:
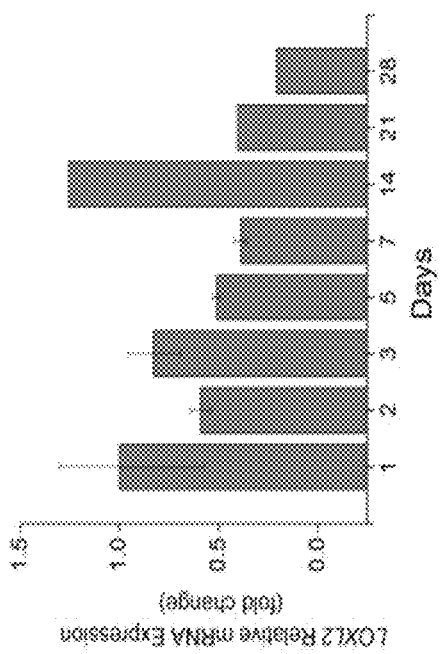
Figure 2B:
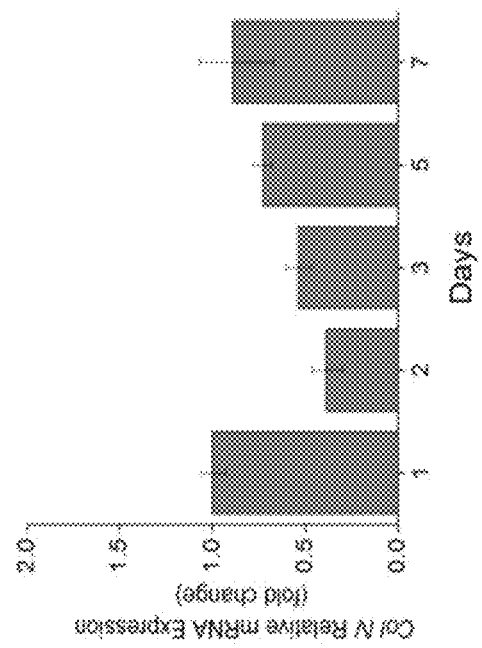
Figure 2C:
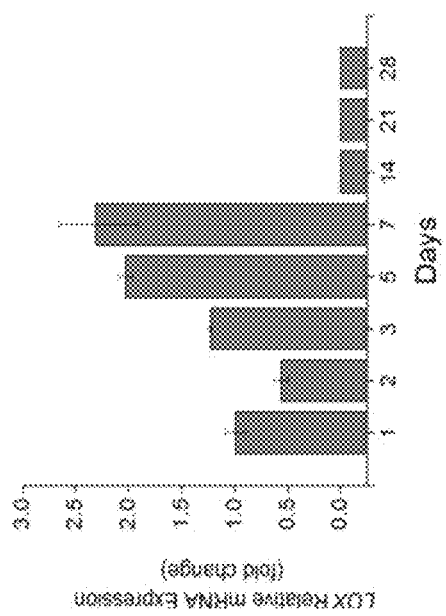
Figure 2D:
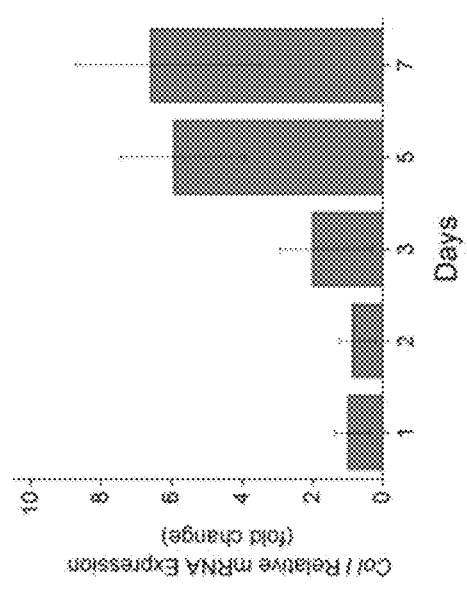

FIGS. 2A-D are graphs illustrating qPCR analysis of LOX (FIG. 2A), LOXL2 (FIG. 2B), Collagen I (FIG. 2C) and Collagen IV (FIG. 2D).

Figure 3A:
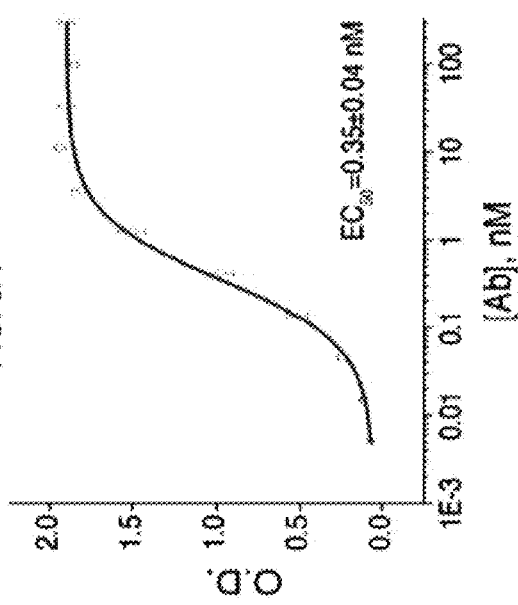
Figure 3B:
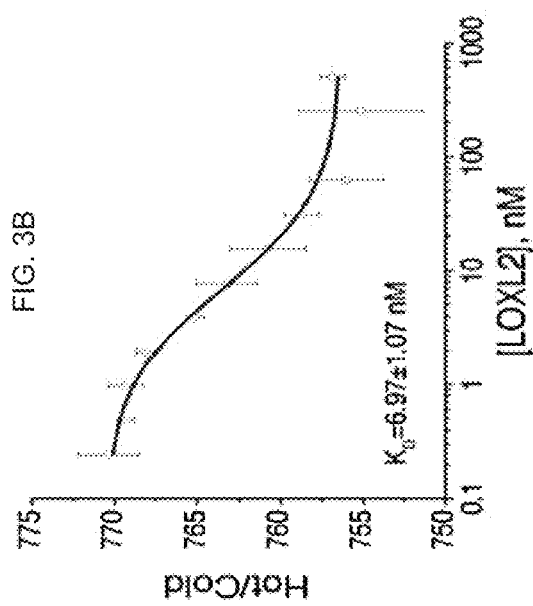
Figure 3C:
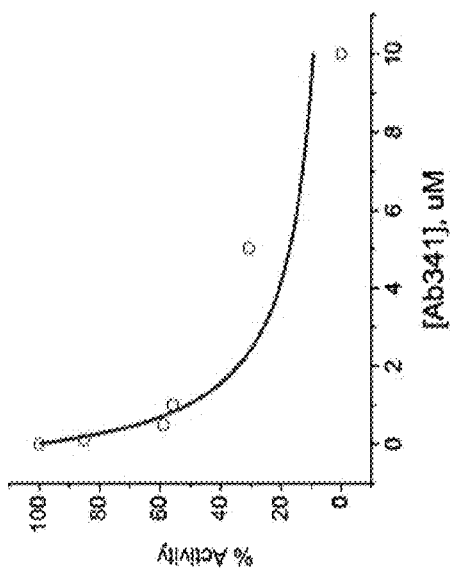

FIGS. 3A-C GS341 is a nanomolar binder of LOXL2 and inhibits LOXL2 enzymatic activity. A) ELISA assay for GS341 binding to the catalytic domains of LOXL2. B) Binding analysis in solution by microscale thermophoresis. Values on the Y-axis represent the percentage of the maximal thermophoretic response observed, or in the case of no detectable binding values on the Y-axis represent the thermophoretic shift of the labeled protein. All binding curves were determined in triplicate by MST and are represented as the mean±SD. Error bars represent standard deviation of representative experiments done in triplicate. C) Inhibition of collagen cross-linking by GS341.

FIGS. 4A-F Inhibition of LOXL2 by GS341 changes the morphology of ECM secreted by fibroblast cells. A) 3D spheroid invasion assay of MDA-231 cells through Matrigel in the presence of vehicle or GS341 (10 uM) demonstrated reduction in invasion by 70% upon treatment with GS341. B) Representative SHG images of control and GS341 treated fibroblasts demonstrate wavy-like organization of collagen fibers in the control samples, while treatment Scale bar 50 uM. C) Raman (scale bar 10 uM) analyses of ECM derived from the fibroblast grown in the presence of PBS or GS341 (100 ngr) for four weeks, demonstrate dramatic differences in collagen morphology. D) MS analysis of ECM derived from the control and GS341 treated cells did not detect statistically significant differences in ECM composition indicating that GS341 affects only ECM morphology (The scale represent relative fold change within each protein compared with the other group). E) SEM analysis of nanoscale changes in collagen fiber morphology upon treatment with GS341 of same sample as in B. F) Fibril orientation analysis of the fibrils done by Fiji. Inhibition of collagen cross-linking by GS341 led to multi-oriented fibril organization.

FIG. 5A Representative two-photon SHG images of collagen secreted by human dermal fibroblast treated with PBS at various time points, depicting collagen synthesis (day 5), assembly into linear fibrils (day 7) and maturation into cross-linked collagen fibers (4 weeks). Scale bar 50 μm.

Figure 5B:
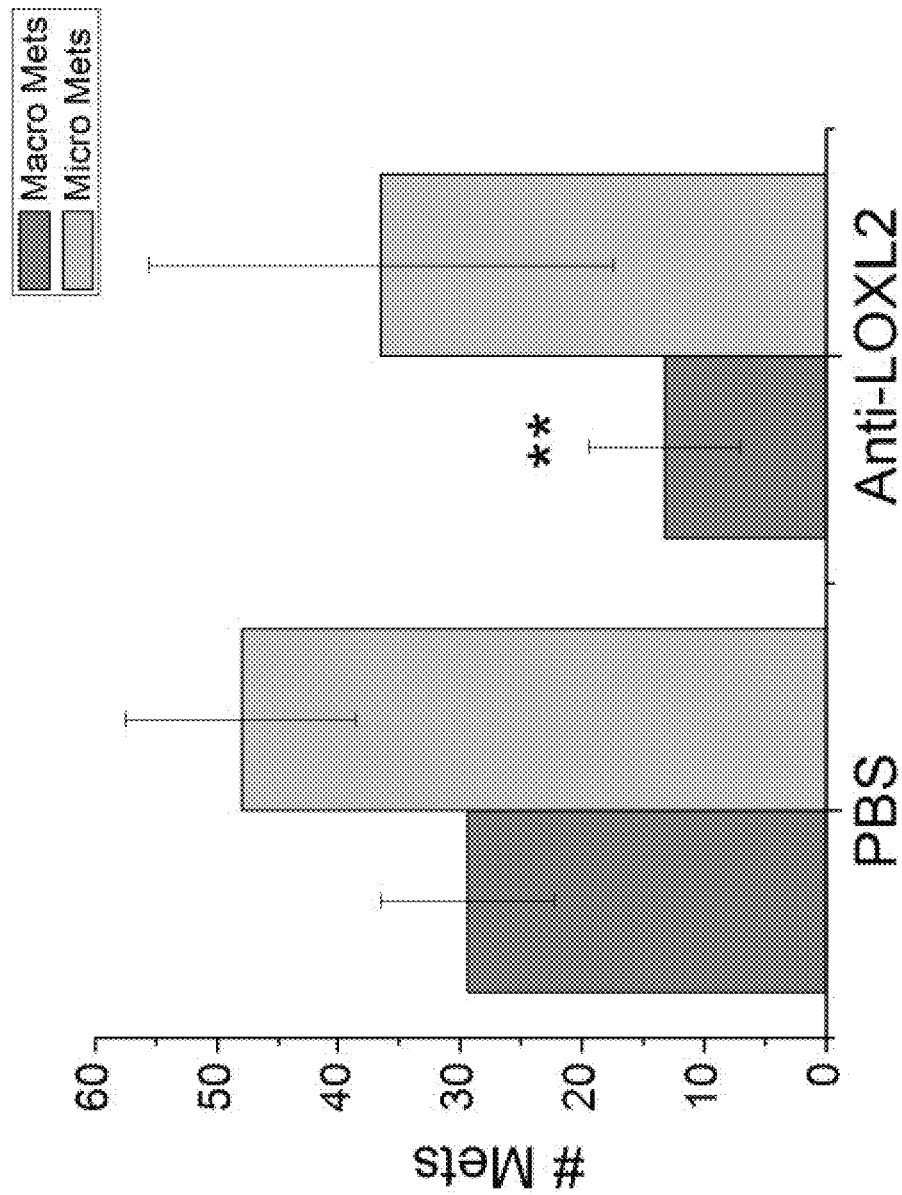
Figure 6:
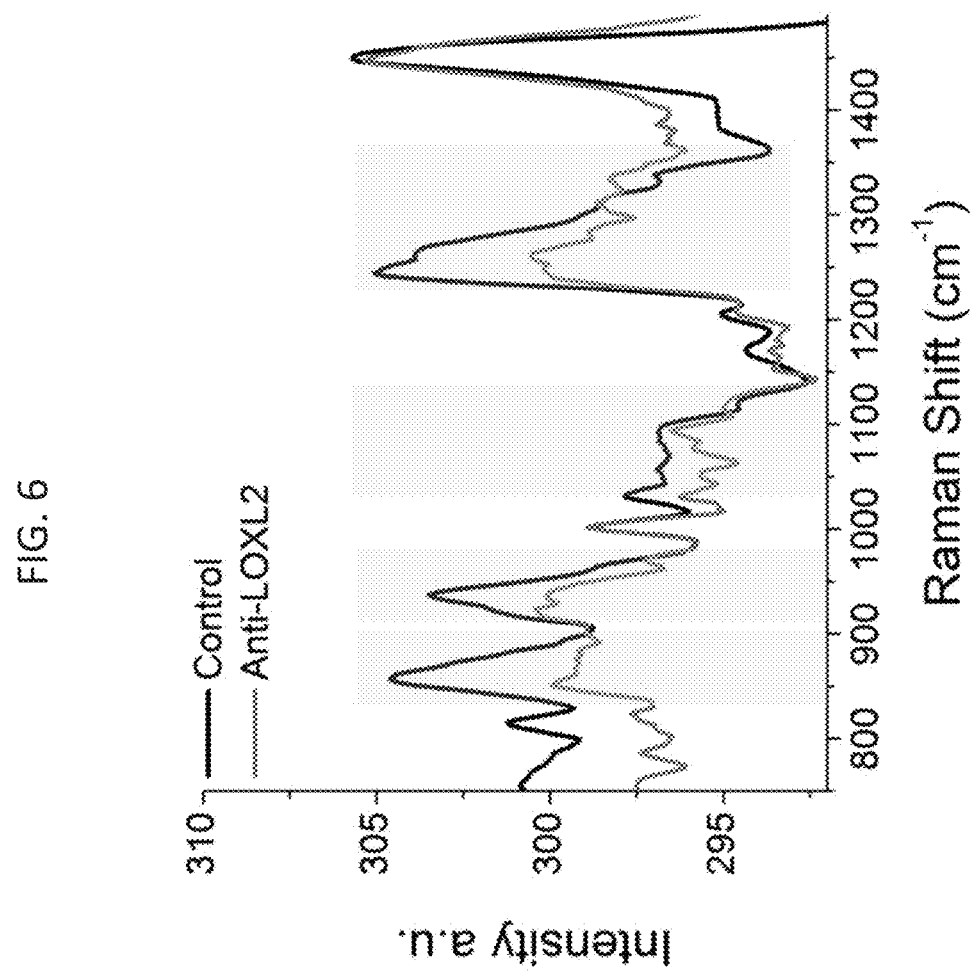

FIG. 5B SHG images of cells treated with 100 ngr GS341 did not mature into crosslinked collagen fibers as in FIG. 5A (4 weeks), but remained linear, FIG. 6 is a Raman spectra for a non-treated and GS341 treated decellularized ECM sample, demonstrating differences in collagen bond chemistry.

FIGS. 7A-H De-remodeling of the tumor ECM reduces metastasis seeding to the lungs. A) Treatment with GS341 (30 mg/kg) reduce tumor size in experimental metastasis model in which MDA-231 cells are implanted into the mammary fatpad of mice after 8 weeks (n=4 for each group), P*<0.05. B) Quantification of lung metastases formed after orthotopic injection of MDA-MB-231 cells. Mice were either untreated or treated with GS341. n=5 mice per group. C) Inhibition by GS341 reduced tumor cell proliferation in vivo demonstrated by immunofluorescence staining for phosphohistone h3 (ph3) of paraffin tumor sections P*<0.05. D) Mass spectrometry analysis of ECM from tumors reveal changes in ECM composition (n=2 per group). E) Representative SHG imaging of collagen of the tumors demonstrate a shift from linear collagen organization of the vehicle treated tumors into random orientation upon treatment with GS341. F) Analysis of fiber orientation. G) SEM analysis of nanoscale changes in collagen fiber morphology upon treatment with GS341 are similar to that observed for the fibroblast cells (2E). H) Quantification of fibril diameter by ImageJ depicts a shift to thinner fibrils upon treatment with GS341 (n=100) P***<0.0001. * Difference from a previous time point is statistically significant with P<0.0001. Error bars represent standard error of the mean of 20 images. n=2 animals for each time point. Scale bar represents 25 μm.

Figure 8B:
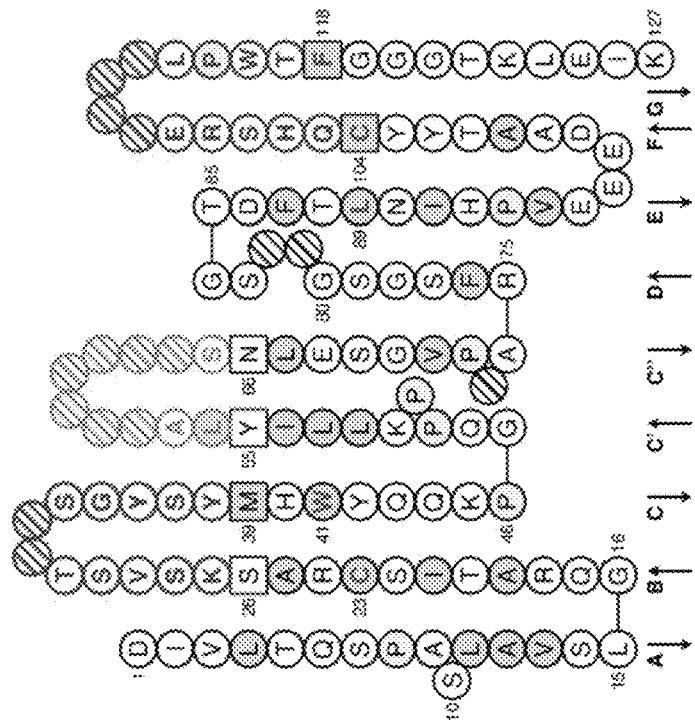
Figure 8A:
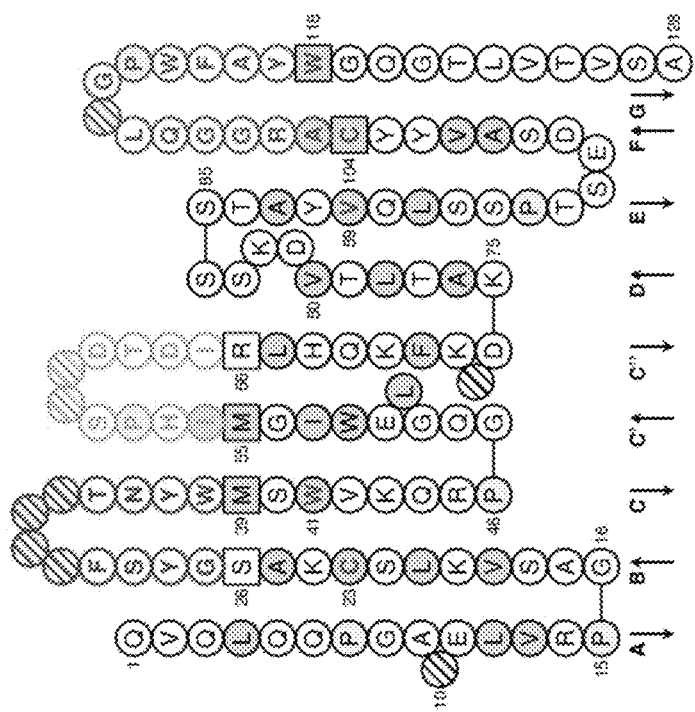

FIGS. 8A-B is a schematic illustration of the sequence of the VH (FIG. 8A-SEQ ID NO: 1) and VL (FIG. 8B-SEQ ID NO: 2).

FIGS. 9A-C is a tube formation assay demonstrating that treatment with GS341 reduces the number of nodes formed by endothelial cells during formation of tubes.

FIGS. 9D-F is a 2D invasion assay of MDA-MB-231 cells through matrigel in the presence of control antibody and GS341. Treatment with GS341 reduce cell invasion by 50%.

Figure 9H:
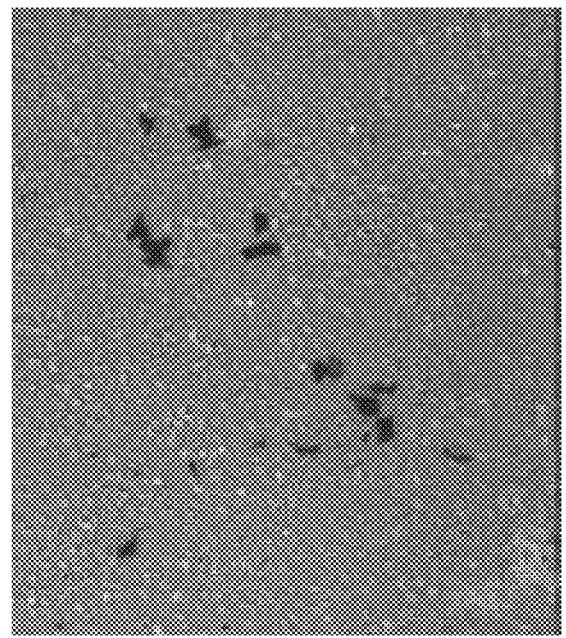
Figure 9G:
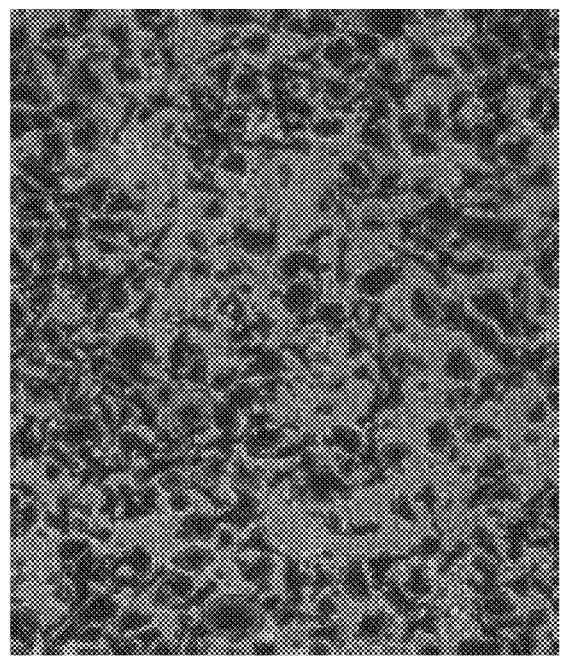

FIGS. 9G-H is a 2D invasion assay of MDA-MB-231 cells through matrigel in the presence of control antibody and a combination of GS341 and anti-MMP-9 antibody.

FIGS. 10A-E CCL4 mice model of liver metastasis. CCL4 is injected into mice. Fibrosis picks up after 24 hours. Thick branched collagen forms in the liver. TIMP is elevated after 24 hours and inhibits collagenases (FIG. 10E). The tissue is stained with Sirius red collagen stain. From 72 hours, the tissue regenerates-loss of red stain (FIGS. 10A-D).

Figure 11B:
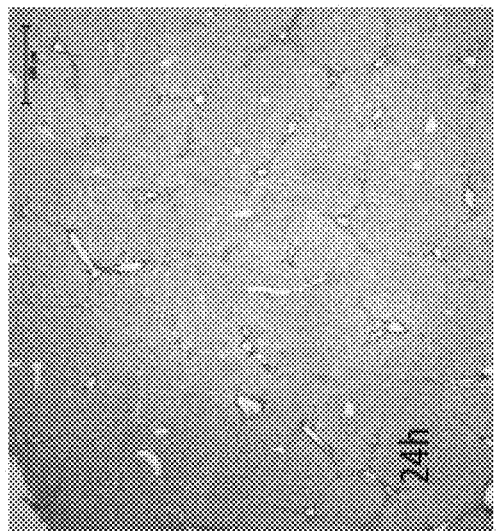
Figure 11C:
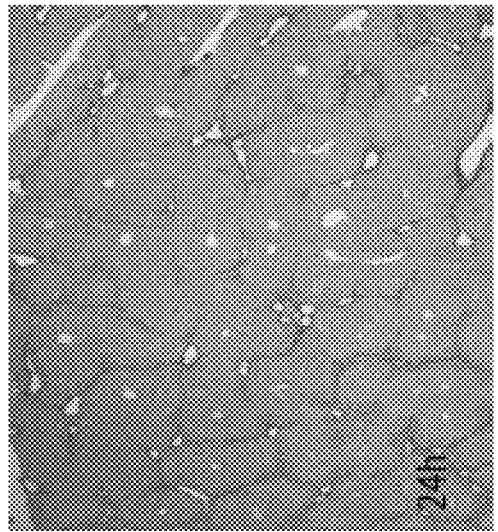
Figure 11A:
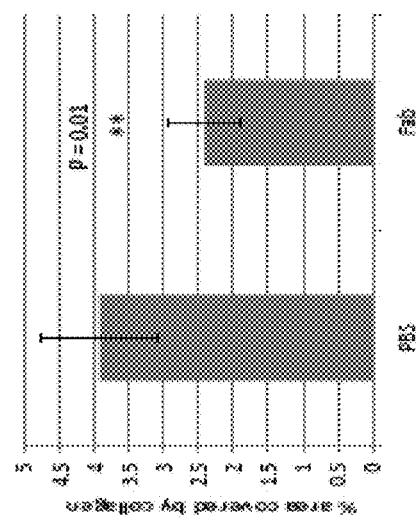

FIGS. 11A-C Treatment of CCL4 mice with GS341 significantly attenuates fibrosis (loss of red stain) resulting in a speeding up of tissue regeneration.

Figure 12A:
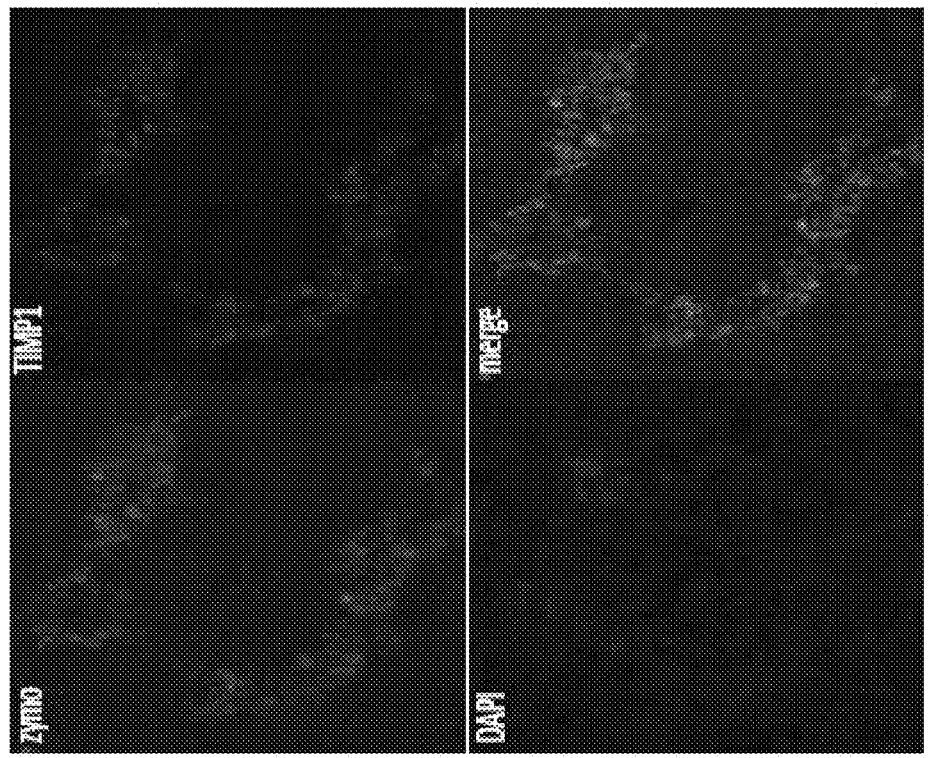
Figure 12B:
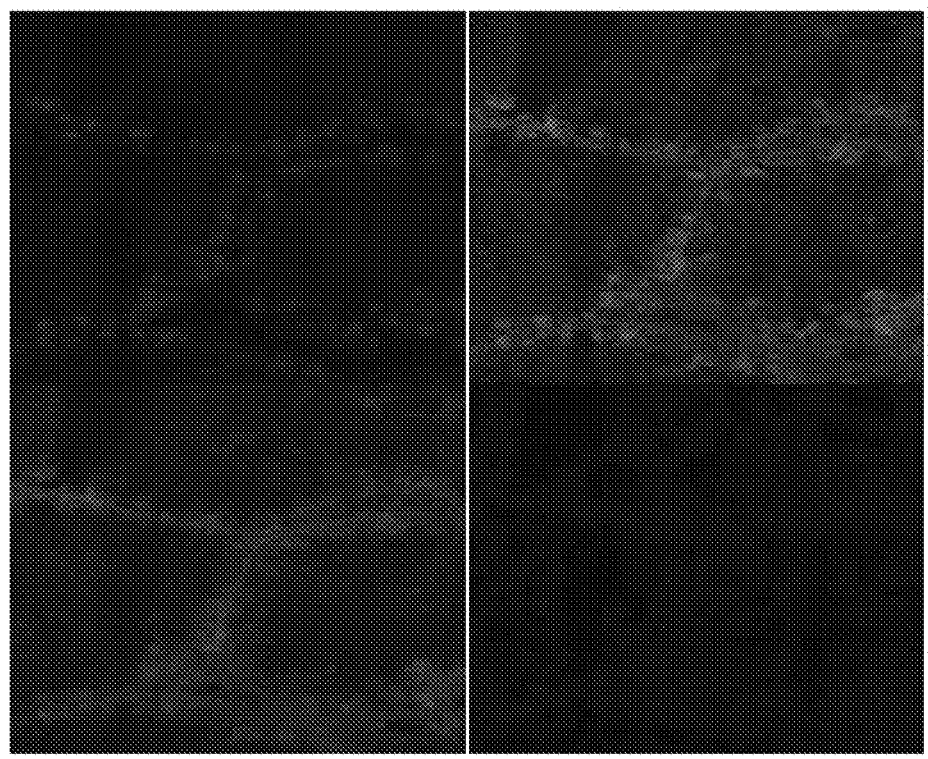

FIGS. 12A-B Treatment with Fab GS341 provides access of collagenases (possibly from immune cells) to the collagen fibrotic scar. Green-tissue collagen zymography indicative of collagenase activity in the tissue red-staining of TIMPs (endogenous MMP inhibitors) and blue-DAPI. Note the TIMP signal is not localized on the scarred fibers in the treated tissue which means no interference with collagenase activity during treatment with GS341 (possibly secreted from different cells).

DESCRIPTION OF SPECIFIC EMBODIMENTS OF THE INVENTION

The present invention, in some embodiments thereof, relates to antibodies targeted against lysyl-oxidase like protein-2 (LOXL-2) which are capable of altering the architecture of pathologocial collagen assembly.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The extracellular medium (ECM) is an extremely versatile biomaterial regulating intricately cell-cell connections, interactions and communications. Tissue stiffness via remodeling of collagen, a major component of the ECM, is often linked with pathological scenarios including fibrosis and poor prognosis in several solids tumors.

The present inventors characterized ECM synthesis, assembly and maturation by human dermal fibroblast which served as a model system for stromal ECM. By characterizing LOX/LOXL2 expression levels profiles, the present inventors found that LOXL2 is involved in the later stages of covalent collagen assembly (FIGS. 1A-B). The present inventors targeted the enzymatic activity of LOXL-2 at the ECM by developing an inhibitory monoclonal antibody of LOXL-2. They screened for antibodies that demonstrates a direct effect on ECM architecture. This effect was quantified by an integrated spectroscopic approach involving two photon second harmonic generation, raman microspectroscopy and scanning electron microscopy (FIGS. 4A-F, 5A, 6 and 7A-H). The ECM interfering antibody demonstrated therapeutic potential in mice models of breast cancer metastasis (FIG. 5B), by inducing morphological changes in collagen fibers organization in the primary tumor crucial for cancer cell invasion and metastasis (FIGS. 9A-H, 10A-E and 11A-C).

The results demonstrate shifts of cancerous collagen linearization to random orientation distribution which led to significant decrease of primary tumor progression and attenuation of lung metastasis via collagen disassembly mechanisms. Altogether the present results highlight LOXL-2 antibodies as effective inhibitors targeting pathological collagen assembly. These inhibitors may be used as primary inhibitors, as well as in adjuvant therapy for cancer, fibrosis and other collagen based pathologies.

Thus, according to one aspect of the present invention there is provided an agent which down-regulates the activity and/or expression of lysyl-oxidase like protein-2 (LOXL-2) and which is capable of altering the structure of the extracellular matrix.

The term "lysyl-oxidase like protein-2 (LOXL-2)" refers to human LOXL-2 having the EC 1.4.3.13, which has a collagen crosslinking activity and has an amino acid sequence at least 90% homologous, at least 91% homologous, at least 92% homologous, at least 93% homologous, at least 94% homologous, at least 95% homologous, at least 96% homologous, at least 97% homologous, at least 98% homologous, at least 99% homologous, and more preferably 100% homologous to the amino acid sequence as set forth in SEQ ID NO: 9.

The agents of this aspect of the present invention are capable of specifically binding LOXL-2 or at least a part of the LOXL-2 protein or DNA or mRNA encoding same. According to a particular embodiment, the agents bind to a region spanning the catalytic site of LOXL-2 (or DNA or mRNA encoding same) and inhibiting its activity when introduced into the mammalian tissue.

According to a particular embodiment, the agents are capable of down-regulating crosslinking of type I collagen in an in vitro assay system as further described in Example 1 herein below. Further, the agents are capable of down-regulating crosslinking of pathological (or aberrant) type I collagen in vivo following administration. Thus, for example, the present inventors contemplate antibodies which down-regulate the crosslinking activity of type I collagen with an $IC_{50}$ between 1 nM-10 µM. More preferably between 1 nM-1 µM. According to a specific embodiment, the antibody down-regulates the crosslinking activity of type I collagen with an $IC_{50}$ with an $IC_{50}$ of about 1 µM.

Since the agents of this aspect of the present invention are capable of interfering with type I collagen crosslinking, they alter the structure of the extracellular matrix (ECM), relaxing the collagen fibers, changing them from an ordered orientation to a more random orientation. Thus, the agents of this aspect of the present invention alter the fibrillation of collagen (and accordingly strength of the collagen) without affecting the amount of collagen.

Methods of analyzing collagen architecture are known in the art and include for example second harmonic generation (SHG) microscopy, electron microscopy imaging and Raman microscopy.

According to another embodiment, the agents of this aspect of the present invention do not affect angiogenesis in vivo.

For example, the Cultrex® Directed In Vivo Angiogenesis Assay (DIVAA™) may be performed. During the course of the assay, implant grade silicone cylinders closed at one end, called angioreactors, are filled with basement membrane extract (BME) premixed with or without angiogenesis modulating factors. These angioreactors are then implanted subcutaneously in the dorsal flanks of nude mice. If filled with angiogenic factors, vascular endothelial cells migrate into, and proliferate in the BME to form vessels in the angioreactor. As early as nine days post-implantation, there are enough cells to determine an effective dose response to angiogenic factors.

One example, of an agent capable of downregulating LOXL-2 is an antibody or antibody fragment capable of specifically binding LOXL-2. Preferably, the antibody specifically binds at least one epitope of LOXL-2 (e.g. the catalytic domain). Thus, for example the antibody may bind to residues 545-775 of LOXL-2.

As used herein, the term "binding" or "specifically binding" refers to the binding of the antibody to an epitope of the antigen (either VEGF or ANG2) in an in-vitro assay, e.g. in an ELISA assay or in a surface plasmon resonance assay (BIAcore, GE-Healthcare Uppsala, Sweden or BIO-RAD ProteOn XPR36) with purified wild-type antigen. The affinity of the binding is defined by the terms Ka (rate constant for the association of the antibody from the antibody/antigen complex), kD (dissociation constant), and KD (kD/ka).

Preferably, the antibody binds with an affinity less than $10 \times 10^{-9}$ mol/l, more preferably less than $9 \times 10^{-9}$ mol/l, more preferably less than $8 \times 10^{-9}$ mol/l, more preferably less than $7 \times 10^{-9}$ mol/l, more preferably less than $6 \times 10^{-9}$ mol/l, more preferably less than $5 \times 10^{-9}$ mol/l, more preferably less than $4 \times 10^{-9}$ mol/l, more preferably less than $3 \times 10^{-9}$ mol/l, more preferably less than $2 \times 10^{-9}$ mol/l, and more preferably less than $1 \times 10^{-9}$ mol/l. Preferably the antibody binds with an affinity between preferably $10^{-9}$ M to $10^{-13}$ mol/l.

As used herein, the term "epitope" refers to any antigenic determinant on an antigen to which the paratope of an antibody binds.

According to a particular embodiment, the antibody binds the catalytic site of the LOXL-2 protein (situated between residues 545-775) with at least 2 fold higher, 5 fold higher, 10 fold higher, or even 20 fold higher affinity than to the fourth scavenger receptor-cysteine-rich (SRCR) domain of LOXL-2 (situated between residues 435-544).

According to still another embodiment, the antibody doesn't bind to the fourth scavenger receptor-cysteine-rich (SRCR) domain of LOXL-2 (situated between residues 435-544).

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

As used herein "recombinant antibody" refers to intact antibodies that are prepared, expressed, created or isolated by recombinant means, such as (a) antibodies isolated from an animal (e.g., mouse) that is transgenic for immunoglobulin genes (e.g., human immunoglobulin genes) or hybridoma prepared therefrom; (b) antibodies isolated from a host cell (e.g. prokaryotic cells) transformed to express the antibody; (c) antibodies isolated from a recombinant antibody library; and (d) antibodies prepared, expressed, created or isolated by any other means that involve splicing of immunoglobulin gene sequences to other DNA sequences. In certain embodiments immunoglobulin of the present invention may have variable and constant regions derived from human germline immunoglobulin sequences. In other embodiments, such recombinant human antibodies can be subjected to in vitro mutagenesis and thus the amino acid sequences of the $V_H$ and $V_L$ regions of the recombinant antibodies comprise sequences that while derived from and related to human germline $V_H$ and $V_L$ sequences, may not naturally exist within the human antibody germline repertoire in vivo.

The following exemplary embodiments of antibodies (both monospecific and bispecific) are encompassed by the scope of the invention.

As used herein "human antibody" refers to intact antibodies having variable regions in which both the framework and CDR regions are derived from human immunoglobulin sequences as described, for example, by Kabat et al. (see Kabat 1991, Sequences of proteins of immunological Interest, $5^{th}$ Ed. NIH Publication No. 91-3242). The constant region of the human antibody is also described from human immunoglobulin sequences. The human antibodies may include amino residues not encoded by human germline immunoglobulin sequences (e.g., mutations introduced by random or site directed mutagenesis in vitro or somatic mutation in vivo). However, the term "human antibody", as used herein, is not intended to include antibodies in which CDR sequences derived from the germline of another mammalian species, such as a mouse, have been grafted onto human framework sequences.

As used herein, a "chimeric antibody" refers to an intact antibody in which the variable regions derive from a first species and the constant regions are derived from a second species. Chimeric immunoglobulins can be constructed by genetic engineering from immunoglobulin gene segments belonging to different species (e.g., VH and VL domains from a mouse antibody with constant domains of human origin).

As used herein "humanized immunoglobulin" refers to an intact antibody in which the minimum mouse part from a non-human (e.g., murine) antibody is transplanted onto a human antibody; generally humanized antibodies are 5-10% mouse and 90-95% human.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to specific embodiments, the antibody of this aspect of the present invention comprises CDR sequences as set forth in SEQ ID NOs: 3-8.

According to other embodiments, the amino acid sequence of the $V_H$ of the antibody is at least 90% identical to SEQ ID NO: 1, more preferably at least 91% identical to SEQ ID NO: 1, more preferably at least 92% identical to SEQ ID NO: 1, more preferably at least 93% identical to SEQ ID NO: 1, more preferably at least 94% identical to SEQ ID NO: 1, more preferably at least 95% identical to SEQ ID NO: 1, more preferably at least 96% identical to SEQ ID NO: 1, more preferably at least 97% identical to SEQ ID NO: 1, more preferably at least 98% identical to SEQ ID NO: 1, more preferably at least 99% identical to SEQ ID NO: 1, more preferably 100% identical as determined using the Standard protein-protein BLAST [blastp] software of the NCBI to the sequence as set forth in SEQ ID NO: 1, wherein the amino acids of the CDR regions are not replaced by other amino acids.

According to other embodiments, the amino acid sequence of the $V_L$ of the antibody is at least 90% homologous to SEQ ID NO: 2, more preferably at least 91% homologous to SEQ ID NO: 2, more preferably at least 92% homologous to SEQ ID NO: 2, more preferably at least 93% homologous to SEQ ID NO: 2, more preferably at least 94% homologous to SEQ ID NO: 2, more preferably at least 95% homologous to SEQ ID NO: 2, more preferably at least 96% homologous to SEQ ID NO: 2, more preferably at least 97% homologous to SEQ ID NO: 2, more preferably at least 98% homologous to SEQ ID NO: 2, more preferably at least 99% homologous to SEQ ID NO: 2, more preferably 100% homologous as determined using the Standard protein-protein BLAST [blastp] software of the NCBI to the sequence as set forth in SEQ ID NO: 2, wherein the amino acids of the CDR regions are not replaced by other amino acids.

The antibodies of the present invention may be conjugated to a functional moiety such as a detectable or a therapeutic moiety.

Various types of detectable or reporter moieties may be conjugated to the antibody of the invention. These include, but not are limited to, a radioactive isotope (such as [125]

iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomagraphy (PET) or Magnetic Resonance Imaging (MRI).

Table 1 provides non-limiting examples of identifiable moieties which can be conjugated to the antibody of the invention.

TABLE 1

| Nucleic Acid sequence (GenBank Accession No.) | Amino Acid sequence (GenBank Accession No.) | Identifiable Moiety |
|---|---|---|
| AF435427 | AAL33912 | Green Fluorescent protein |
| AY042185 | AAK73766 | Alkaline phosphatase |
| A00740 | CAA00083 | Peroxidase |
| Nucleotides 790-807 of GenBank Accession No. AF329457 | Amino acids 264-269 of GenBank Accession No. AAK09208 | Histidine tag |
| Nucleotides 817-849 of GenBank Accession No. AF329457 | Amino acids 273-283 of GenBank Accession No. AAK09208 | Myc tag |
| AF435432 | AAL33917 | Biotin lygase tag orange fluorescent protein |
| EU626139 | ACH42114 | Beta galactosidase |
| AF283893 | AAM49066 | Streptavidin |

As mentioned, the antibody may be conjugated to a therapeutic moiety. The therapeutic moiety can be, for example, a cytotoxic moiety, a toxic moiety, a cytokine moiety and a second antibody moiety comprising a different specificity to the antibodies of the invention.

Non-limiting examples of therapeutic moieties which can be conjugated to the antibody of the invention are provided in Table 2, hereinbelow.

TABLE 2

| Nucleic acid sequence (GenBank Accession No.) | Amino acid sequence (GenBank Accession No.) | Therapeutic moiety |
|---|---|---|
| EU090068 | ABU63124 | *Pseudomonas* exotoxin |
| AY820132.1 | AAV70486 | Diphtheria toxin |
| A02159 | CAA00227 | interleukin 2 |
| X03884 | P07766 | CD3 |
| NM_000569.6 | NP_000560.5 | CD16 |
| NM_000589.2 | NP_000580.1 | interleukin 4 |
| K02883 | P01892 | HLA-A2 |
| M57627 | P22301 | interleukin 10 |
| EQ975183 | EEF27734 | Ricin toxin |

The functional moiety may be conjugated to the $V_H$ or the $V_L$ sequence at either the N- or C-terminus or be inserted into other protein sequences in a suitable position.

Downregulation of LOXL-2 can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., SEQ ID NO: 9) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the LOXL-2 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level.

Second, potential target sites are compared to an appropriate genomic database (e.g., human, mouse, rat etc.) using any sequence alignment software, such as the BLAST software available from the NCBI server. Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, a suitable LOXL-2 siRNA can be the siRNA disclosed in US Patent Application No. 20130022617, incorporated herein by reference.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of some embodiments of the invention may be targeted to a bridging region on either side of the deletion. Introduction of such RNA silencing agents into a cell would cause a down-regulation of the mutated protein while leaving the non-mutated protein unaffected.

According to another embodiment the RNA silencing agent may be a miRNA or miRNA mimic.

The term "microRNA", "miRNA", and "miR" are synonymous and refer to a collection of non-coding single-stranded RNA molecules of about 19-28 nucleotides in length, which regulate gene expression. miRNAs are found in a wide range of organisms and have been shown to play a role in development, homeostasis, and disease etiology.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-0,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

Another agent capable of downregulating LOXL-2 is a DNAzyme molecule capable of specifically cleaving an mRNA transcript or DNA sequence of the LOXL-2. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, LM [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www(dot)asgt(dot)org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of LOXL-2 can also be effected by using an antisense polynucleotide capable of specifically hybridizing with an mRNA transcript encoding the LOXL-2.

Design of antisense molecules which can be used to efficiently downregulate a LOXL-2 must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Another agent capable of downregulating LOXL-2 is a ribozyme molecule capable of specifically cleaving an mRNA transcript encoding LOXL-2. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)].

An additional method of regulating the expression of a LOXL-2 gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo | 3'--A | G | G | T |
|-------|-------|---|---|---|
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the LOXL-2 regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003017068 and 20030096980 to Froehler et al, and 20020128218 and 20020123476 to Emanuele et al, and U.S. Pat. No. 5,721,138 to Lawn.

It will be appreciated that since the agent which targets LOXL-2 serves to relax the collagen fibers of the ECM, the present inventors contemplate administering the agent together with an additional agent, whereby the LOXL-2 targeting agent allows the additional agent to gain better access to the site of the disease (e.g. tumor or fibrosis). In this way, it is anticipated that the dose of the additional agent may be lower than the commonly administered dose (i.e. is lower than its effective clinical concentration when administered alone) and accordingly the LOXL-2 targeting agent may serve to lower the side-effects of the additional agent.

In one preferred embodiment, the amount provided of the additional agent of the invention is below the minimum dose required for therapeutic, prophylactic and/or pain palliative effectiveness when used as a single therapy (e.g. 10-99%, preferably 25 to 75% of that minimum dose). This allows for reduction of the side effects caused by the additional agent but the therapy is rendered effective because in combination with the LOXL-2 targeting agent, the additional agents of the invention are effective overall. In a further preferred embodiment the anti-LOXL-2 agents is used at a level below the minimum normal therapeutic dose that brings about angiogenesis, for example 10-99% of the normal minimum therapeutic dose, preferably 25 to 75% of their normal therapeutic dose. This again serves to reduce the danger of side effects and allows a higher level of total effectiveness without exposing the subject to unacceptable side effects.

In one preferred aspect of the present invention, the anti-LOXL-2 agent and the at least one other additional agent of the invention are synergistic with respect to their dosages. That is to say that the effect provided by the anti-LOXL-1 agent of the present invention is greater than would be anticipated from the additive effects of the incorporated doses of anti-LOXL-2 and at least one other additional agent when used separately. In an alternative but equally preferred embodiment, the anti-LOXL-2 agent and the at least one additional agent are synergistic with respect to their side effects. That is to say that the side-effects caused by agents of the present invention are less than would be anticipated when the equivalent therapeutic effect is provided by either anti-LOXL-2 agent or by the additional agent when used separately.

According to embodiments of the present invention, the additional agent is an anti-cancer agent.

According to one embodiment, the anti-cancer agent comprises a chemotherapeutic agent.

Examples of chemotherapeutic agents include but are not limited to abarelix, aldesleukin, aldesleukin, alemtuzumab, alitretinoin, allopurinol, altretamine, amifostine, anastrozole, arsenic trioxide, asparaginase, azacitidine, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dacarbazine, dactinomycin, actinomycin D, Darbepoetin alfa, Darbepoetin alfa, daunorubicin liposomal, daunorubicin, decitabine, Denileukin diftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolone phenpropionate, nelarabine, Nofetumomab, Oprelvekin, Oprelvekin, oxaliplatin, paclitaxel, palifermin, pamidronate, pegademase, pegaspargase, Pegfilgrastim, pemetrexed disodium, pentostatin, pipobroman, plicamycin mithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trastuzumab, tretinoin ATRA, Uracil Mustard, valrubicin, vinblastine, vinorelbine, zoledronate and zoledronic acid.

According to a particular embodiment, the anti-cancer agent is cisplatin.

According to another embodiment, the anti-cancer agent is an antibody.

Examples of antibodies that may be used in the context of the present invention include those listed in Table 3 herein below. It will be appreciated that the present invention contemplates additional antibodies which bind to the targets listed herein below.

TABLE 3

| Name | Target | Use |
| --- | --- | --- |
| 3F8 | GD2 | neuroblastoma |
| 8H9 | B7-H3 | neuroblastoma, sarcoma, metastatic brain cancers |
| Abagovomab | CA-125 (imitation) | ovarian cancer |
| Abciximab | CD41 (integrin alpha-IIb) | platelet aggregation inhibitor |
| Actoxumab | *Clostridium difficile* | *Clostridium difficile* infection |
| Adalimumab | TNF-α | Rheumatoid arthritis, Crohn's Disease, Plaque Psoriasis, Psoriatic Arthritis, Ankylosing Spondylitis, Juvenile Idiopathic Arthritis, Hemolytic disease of the newborn |
| Adecatumumab | EpCAM | prostate and breast cancer |
| Aducanumab | beta-amyloid | Alzheimer's disease |
| Afelimomab | TNF-α | sepsis |
| Afutuzumab | CD20 | lymphoma |
| Alacizumab pegol | VEGFR2 | cancer |
| ALD518 | IL-6 | rheumatoid arthritis |
| Alemtuzumab | CD52 | Multiple sclerosis |
| Alirocumab | NARP-1 | hypercholesterolemia |
| Altumomab pentetate | CEA | colorectal cancer (diagnosis) |
| Amatuximab | mesothelin | cancer |
| Anatumomab mafenatox | TAG-72 | non-small cell lung carcinoma |
| Anifrolumab | interferon α/β receptor | systemic lupus erythematosus |
| Anrukinzumab (=IMA-638) | IL-13 | |
| Apolizumab | HLA-DR | hematological cancers |
| Arcitumomab | CEA | gastrointestinal cancers (diagnosis) |
| Aselizumab | L-selectin (CD62L) | severely injured patients |
| Atinumab | RTN4 | |
| Atlizumab (=tocilizumab) | IL-6 receptor | rheumatoid arthritis |
| Atorolimumab | Rhesus factor | hemolytic disease of the newborn |
| Bapineuzumab | beta amyloid | Alzheimer's disease |
| Basiliximab | CD25 (α chain of IL-2 receptor) | prevention of organ transplant rejections |
| Bavituximab | phosphatidylserine | cancer, viral infections |
| Bectumomab | CD22 | non-Hodgkin's lymphoma (detection) |
| Belimumab | BAFF | non-Hodgkin lymphoma etc. |
| Benralizumab | CD125 | asthma |
| Bertilimumab | CCL11 (eotaxin-1) | severe allergic disorders |
| Besilesomab | CEA-related antigen | inflammatory lesions and metastases (detection) |
| Bevacizumab | VEGF-A | metastatic cancer, retinopathy of prematurity |
| Bezlotoxumab | *Clostridium difficile* | *Clostridium difficile* infection |
| Biciromab | fibrin II, beta chain | thromboembolism (diagnosis) |
| Bimagrumab | ACVR2B | myostatin inhibitor |
| Bivatuzumab mertansine | CD44 v6 | squamous cell carcinoma |
| Blinatumomab | CD19 | cancer |
| Blosozumab | SOST | osteoporosis |
| Brentuximab vedotin | CD30 (TNFRSF8) | hematologic cancers |
| Briakinumab | IL-12, IL-23 | psoriasis, rheumatoid arthritis, inflammatory bowel diseases, multiple sclerosis |
| Brodalumab | IL-17 | inflammatory diseases |
| Canakinumab | IL-1 | rheumatoid arthritis |
| Cantuzumab mertansine | mucin CanAg | colorectal cancer |
| Cantuzumab ravtansine | MUC1 | cancers |
| Caplacizumab | VWF | |
| Capromab pendetide | prostatic carcinoma cells | prostate cancer (detection) |

TABLE 3-continued

| Name | Target | Use |
|---|---|---|
| Carlumab | MCP-1 | oncology/immune indications |
| Catumaxomab | EpCAM, CD3 | ovarian cancer, malignant ascites, gastric cancer |
| CC49 | TAG-72 | tumor detection |
| cBR96-doxorubicin immunoconjugate | Lewis-Y antigen | cancer |
| Cedelizumab | CD4 | prevention of organ transplant rejections, treatment of autoimmune diseases |
| Certolizumab pegol | TNF-α | Crohn's disease |
| Cetuximab | EGFR | metastatic colorectal cancer and head and neck cancer |
| Ch.14.18 | | neuroblastoma |
| Citatuzumab bogatox | EpCAM | ovarian cancer and other solid tumors |
| Cixutumumab | IGF-1 receptor | solid tumors |
| Clazakizumab | *Oryctolagus cuniculus* | rheumatoid arthritis |
| Clenoliximab | CD4 | rheumatoid arthritis |
| Clivatuzumab tetraxetan | MUC1 | pancreatic cancer |
| Conatumumab | TRAIL-R2 | cancer |
| Concizumab | TFPI | bleeding |
| Crenezumab | 1-40-β-amyloid | Alzheimer's disease |
| CR6261 | Influenza A hemagglutinin | infectious disease/influenza A |
| Dacetuzumab | CD40 | hematologic cancers |
| Daclizumab | CD25 (α chain of IL-2 receptor) | prevention of organ transplant rejections |
| Dalotuzumab | insulin-like growth factor I receptor | cancer etc. |
| Daratumumab | CD38 (cyclic ADP ribose hydrolase) | |
| Demcizumab | DLL4 | cancer |
| Denosumab | RANKL | osteoporosis, bone metastases etc. |
| Detumomab | B-lymphoma cell | lymphoma |
| Dorlimomab aritox | | |
| Drozitumab | DR5 | cancer |
| Duligotumab | HER3 | |
| Dupilumab | IL4 | atopic diseases |
| Dusigitumab | ILGF2 | cancer |
| Ecromeximab | GD3 ganglioside | malignant melanoma |
| Eculizumab | C5 | paroxysmal nocturnal hemoglobinuria |
| Edobacomab | endotoxin | sepsis caused by Gram-negative bacteria |
| Edrecolomab | EpCAM | colorectal carcinoma |
| Efalizumab | LFA-1 (CD11a) | psoriasis (blocks T-cell migration) |
| Efungumab | Hsp90 | invasive *Candida* infection |
| Eldelumab | interferon gamma-induced protein | Crohn's disease, ulcerative colitis |
| Elotuzumab | SLAMF7 | multiple myeloma |
| Elsilimomab | IL-6 | |
| Enavatuzumab | TWEAK receptor | cancer |
| Enlimomab pegol | ICAM-1 (CD54) | |
| Enokizumab | IL9 | asthma |
| Enoticumab | DLL4 | |
| Ensituximab | 5AC | cancer |
| Epitumomab cituxetan | episialin | |
| Epratuzumab | CD22 | cancer, SLE |
| Erlizumab | ITGB2 (CD18) | heart attack, stroke, traumatic shock |
| Ertumaxomab | HER2/neu, CD3 | breast cancer etc. |
| Etaracizumab | integrin $\alpha_v\beta_3$ | melanoma, prostate cancer, ovarian cancer etc. |
| Etrolizumab | integrin $\alpha_7\beta_7$ | inflammatory bowel disease |
| Evolocumab | PCSK9 | hypocholesterolemia |
| Exbivirumab | hepatitis B surface antigen | hepatitis B |
| Fanolesomab | CD15 | appendicitis (diagnosis) |
| Faralimomab | interferon receptor | |
| Farletuzumab | folate receptor 1 | ovarian cancer |
| Fasinumab | HNGF | |
| FBTA05 | CD20 | chronic lymphocytic leukaemia |
| Felvizumab | respiratory syncytial virus | respiratory syncytial virus infection |
| Fezakinumab | IL-22 | rheumatoid arthritis, psoriasis |
| Ficlatuzumab | HGF | cancer etc. |
| Figitumumab | IGF-1 receptor | adrenocortical carcinoma, non-small cell lung carcinoma etc. |
| Flanvotumab | TYRP1(glycoprotein 75) | melanoma |

TABLE 3-continued

| Name | Target | Use |
|---|---|---|
| Fontolizumab | IFN-γ | Crohn's disease etc. |
| Foralumab | CD3 epsilon | |
| Foravirumab | rabies virus glycoprotein | rabies (prophylaxis) |
| Fresolimumab | TGF-β | idiopathic pulmonary fibrosis, focal segmental glomerulosclerosis, cancer |
| Fulranumab | NGF | pain |
| Futuximab | EGFR | |
| Galiximab | CD80 | B-cell lymphoma |
| Ganitumab | IGF-I | cancer |
| Gantenerumab | beta amyloid | Alzheimer's disease |
| Gavilimomab | CD147 (basigin) | graft versus host disease |
| Gemtuzumab ozogamicin | CD33 | acute myelogenous leukemia |
| Gevokizumab | IL-1β | diabetes. |
| Girentuximab | carbonic anhydrase 9 (CA-IX) | clear cell renal cell carcinoma[64] |
| Glembatumumab vedotin | GPNMB | melanoma, breast cancer |
| Golimumab | TNF-α | rheumatoid arthritis, psoriatic arthritis, ankylosing spondylitis |
| Gomiliximab | CD23 (IgE receptor) | allergic asthma |
| Guselkumab | IL13 | psoriasis |
| Ibalizumab | CD4 | HIV infection |
| Ibritumomab tiuxetan | CD20 | non-Hodgkin's lymphoma |
| Icrucumab | VEGFR-1 | cancer etc. |
| Igovomab | CA-125 | ovarian cancer (diagnosis) |
| IMAB362 | CLDN18.2 | gastrointestinal adenocarcinomas and pancreatic tumor |
| Imciromab | cardiac myosin | cardiac imaging |
| Imgatuzumab | EGFR | cancer |
| Inclacumab | selectin P | |
| Indatuximab ravtansine | SDC1 | cancer |
| Infliximab | TNF-α | rheumatoid arthritis, ankylosing spondylitis, psoriatic arthritis, psoriasis, Crohn's disease, ulcerative colitis |
| Intetumumab | CD51 | solid tumors (prostate cancer, melanoma) |
| Inolimomab | CD25 (α chain of IL-2 receptor) | graft versus host disease |
| Inotuzumab ozogamicin | CD22 | cancer |
| Ipilimumab | CD152 | melanoma |
| Iratumumab | CD30 (TNFRSF8) | Hodgkin's lymphoma |
| Itolizumab | CD6 | |
| Ixekizumab | IL-17A | autoimmune diseases |
| Keliximab | CD4 | chronic asthma |
| Labetuzumab | CEA | colorectal cancer |
| Lambrolizumab | PDCD1 | antineoplastic agent |
| Lampalizumab | CFD | |
| Lebrikizumab | IL-13 | asthma |
| Lemalesomab | NCA-90 (granulocyte antigen) | diagnostic agent |
| Lerdelimumab | TGF beta 2 | reduction of scarring after glaucoma surgery |
| Lexatumumab | TRAIL-R2 | cancer |
| Libivirumab | hepatitis B surface antigen | hepatitis B |
| Ligelizumab | IGHE | |
| Lintuzumab | CD33 | cancer |
| Lirilumab | KIR2D | |
| Lodelcizumab | PCSK9 | hypercholesterolemia |
| Lorvotuzumab mertansine | CD56 | cancer |
| Lucatumumab | CD40 | multiple myeloma, non-Hodgkin's lymphoma, Hodgkin's lymphoma |
| Lumiliximab | CD23 (IgE receptor) | chronic lymphocytic leukemia |
| Mapatumumab | TRAIL-R1 | cancer |
| Margetuximab | ch4D5 | cancer |
| Maslimomab | T-cell receptor | |
| Mavrilimumab | GMCSF receptor α-chain | rheumatoid arthritis |
| Matuzumab | EGFR | colorectal, lung and stomach cancer |
| Mepolizumab | IL-5 | asthma and white blood cell diseases |
| Metelimumab | TGF beta 1 | systemic scleroderma |
| Milatuzumab | CD74 | multiple myeloma and other hematological malignancies |

TABLE 3-continued

| Name | Target | Use |
|---|---|---|
| Minretumomab | TAG-72 | |
| Mitumomab | GD3 ganglioside | small cell lung carcinoma |
| Mogamulizumab | CCR4 | cancer |
| Morolimumab | Rhesus factor | |
| Motavizumab | respiratory syncytial virus | respiratory syncytial virus (prevention) |
| Moxetumomab pasudotox | CD22 | cancer |
| Muromonab-CD3 | CD3 | prevention of organ transplant rejections |
| Nacolomab tafenatox | C242 antigen | colorectal cancer |
| Namilumab | CSF2 | |
| Naptumomab estafenatox | 5T4 | non-small cell lung carcinoma, renal cell carcinoma |
| Narnatumab | RON | cancer |
| Natalizumab | integrin $\alpha_4$ | multiple sclerosis, Crohn's disease |
| Nebacumab | endotoxin | sepsis |
| Necitumumab | EGFR | non-small cell lung carcinoma |
| Nerelimomab | TNF-$\alpha$ | |
| Nesvacumab | angiopoietin 2 | cancer |
| Nimotuzumab | EGFR | squamous cell carcinoma, head and neck cancer, nasopharyngeal cancer, glioma |
| Nivolumab | IgG4 | cancer |
| Nofetumomab merpentan | | cancer (diagnosis) |
| Ocaratuzumab | CD20 | cancer |
| Ocrelizumab | CD20 | rheumatoid arthritis, lupus erythematosus etc. |
| Odulimomab | LFA-1 (CD11a) | prevention of organ transplant rejections, immunological diseases |
| Ofatumumab | CD20 | chronic lymphocytic leukemia etc. |
| Olaratumab | PDGF-R $\alpha$ | cancer |
| Olokizumab | IL6 | |
| Omalizumab | IgE Fc region | allergic asthma |
| Onartuzumab | human scatter factor receptor kinase | cancer |
| Ontuxizumab | TEM1 | cancer |
| Oportuzumab monatox | EpCAM | cancer |
| Oregovomab | CA-125 | ovarian cancer |
| Orticumab | oxLDL | |
| Otelixizumab | CD3 | diabetes mellitus type 1 |
| Otlertuzumab | CD37 | cancer |
| Oxelumab | OX-40 | asthma |
| Ozanezumab | NOGO-A | ALS and multiple sclerosis |
| Ozoralizumab | TNF-$\alpha$ | inflammation |
| Pagibaximab | lipoteichoic acid | sepsis (*Staphylococcus*) |
| Palivizumab | F protein of respiratory syncytial virus | respiratory syncytial virus (prevention) |
| Panitumumab | EGFR | colorectal cancer |
| Pankomab | tumor specific glycosylation of MUC1 | ovarian cancer |
| Panobacumab | *Pseudomonas aeruginosa* | *Pseudomonas aeruginosa* infection |
| Parsatuzumab | EGFL7 | cancer |
| Pascolizumab | IL-4 | asthma |
| Pateclizumab | LTA | TNF |
| Patritumab | HER3 | cancer |
| Pemtumomab | MUC1 | cancer |
| Perakizumab | IL17A | arthritis |
| Pertuzumab | HER2/neu | cancer |
| Pexelizumab | C5 | reduction of side effects of cardiac surgery |
| Pidilizumab | PD-1 | cancer and infectious diseases |
| Pinatuzumab vedotin | CD22 | cancer |
| Pintumomab | adenocarcinoma antigen | adenocarcinoma (imaging) |
| Placulumab | human TNF | |
| Polatuzumab vedotin | CD79B | |
| Ponezumab | human beta-amyloid | Alzheimer's disease |
| Priliximab | CD4 | Crohn's disease, multiple sclerosis |
| Pritoxaximab | *E. coli* shiga toxin type-1 | |
| Pritumumab | vimentin | brain cancer |
| PRO 140 | CCR5 | HIV infection |

TABLE 3-continued

| Name | Target | Use |
|---|---|---|
| Quilizumab | IGHE | |
| Racotumomab | N-glycolylneuraminic acid | cancer |
| Radretumab | fibronectin extra domain-B | cancer |
| Rafivirumab | rabies virus glycoprotein | rabies (prophylaxis) |
| Ramucirumab | VEGFR2 | solid tumors |
| Ranibizumab | VEGF-A | macular degeneration (wet form) |
| Raxibacumab | anthrax toxin, protective antigen | anthrax (prophylaxis and treatment) |
| Regavirumab | cytomegalovirus glycoprotein B | cytomegalovirus infection |
| Reslizumab | IL-5 | inflammations of the airways, skin and gastrointestinal tract |
| Rilotumumab | HGF | solid tumors |
| Rituximab | CD20 | lymphomas, leukemias, some autoimmune disorders |
| Robatumumab | IGF-1 receptor | cancer |
| Roledumab | RHD | |
| Romosozumab | sclerostin | osteoporosis |
| Rontalizumab | IFN-α | systemic lupus erythematosus |
| Rovelizumab | CD11, CD18 | haemorrhagic shock etc. |
| Ruplizumab | CD154 (CD40L) | rheumatic diseases |
| Samalizumab | CD200 | cancer |
| Sarilumab | IL6 | rheumatoid arthritis, ankylosing spondylitis |
| Satumomab pendetide | TAG-72 | cancer (diagnosis) |
| Secukinumab | IL-17A | uveitis, rheumatoid arthritis psoriasis |
| Seribantumab | ERBB3 | cancer |
| Setoxaximab | *E. coli* shiga toxin type-1 | |
| Sevirumab | cytomegalovirus | cytomegalovirus infection |
| Sibrotuzumab | FAP | cancer |
| SGN-CD19A | CD19 | acute lymphoblastic leukemia and B-cell non-Hodgkin lymphoma |
| SGN-CD33A | CD33 | Acute myeloid leukemia |
| Sifalimumab | IFN-α | SLE, dermatomyositis, polymyositis |
| Siltuximab | IL-6 | cancer |
| Simtuzumab | LOXL2 | fibrosis |
| Siplizumab | CD2 | psoriasis, graft-versus-host disease (prevention) |
| Sirukumab | IL-6 | rheumatoid arthritis |
| Solanezumab | beta amyloid | Alzheimer's disease |
| Solitomab | EpCAM | |
| Sonepcizumab | sphingosine-1-phosphate | choroidal and retinal neovascularization |
| Sontuzumab | episialin | |
| Stamulumab | myostatin | muscular dystrophy |
| Sulesomab | NCA-90 (granulocyte antigen) | osteomyelitis (imaging) |
| Suvizumab | HIV-1 | viral infections |
| Tabalumab | BAFF | B-cell cancers |
| Tacatuzumab tetraxetan | alpha-fetoprotein | cancer |
| Tadocizumab | integrin $\alpha_{IIb}\beta_3$ | percutaneous coronary intervention |
| Talizumab | IgE | allergic reaction |
| Tanezumab | NGF | pain |
| Taplitumomab paptox | CD19 | cancer |
| Tefibazumab | clumping factor A | *Staphylococcus aureus* infection |
| Telimomab aritox | | |
| Tenatumomab | tenascin C | cancer |
| Teneliximab | CD40 | |
| Teplizumab | CD3 | diabetes mellitus type 1 |
| Teprotumumab | CD221 | hematologic tumors |
| TGN1412 | CD28 | chronic lymphocytic leukemia, rheumatoid arthritis |
| Ticilimumab (= tremelimumab) | CTLA-4 | cancer |
| Tildrakizumab | IL23 | immunologically mediated inflammatory disorders |
| Tigatuzumab | TRAIL-R2 | cancer |
| TNX-650 | IL-13 | Hodgkin's lymphoma |
| Tocilizumab (= atlizumab) | IL-6 receptor | rheumatoid arthritis |
| Toralizumab | CD154 (CD40L) | rheumatoid arthritis, lupus nephritis etc. |

TABLE 3-continued

| Name | Target | Use |
|---|---|---|
| Tositumomab | CD20 | follicular lymphoma |
| Tovetumab | CD140a | cancer |
| Tralokinumab | IL-13 | asthma etc. |
| Trastuzumab | HER2/neu | breast cancer |
| TRBS07 | GD2 | melanoma |
| Tregalizumab | CD4 | |
| Tremelimumab | CTLA-4 | cancer |
| Tucotuzumab celmoleukin | EpCAM | cancer |
| Tuvirumab | hepatitis B virus | chronic hepatitis B |
| Ublituximab | MS4A1 | cancer |
| Urelumab | 4-1BB | cancer etc. |
| Urtoxazumab | *Escherichia coli* | diarrhoea caused by *E. coli* |
| Ustekinumab | IL-12, IL-23 | multiple sclerosis, psoriasis, psoriatic arthritis |
| Vantictumab | Frizzled receptor | cancer |
| Vapaliximab | AOC3 (VAP-1) | |
| Vatelizumab | ITGA2 | |
| Vedolizumab | integrin $\alpha_4\beta_7$ | Crohn's disease, ulcerative colitis |
| Veltuzumab | CD20 | non-Hodgkin's lymphoma |
| Vepalimomab | AOC3 (VAP-1) | inflammation |
| Vesencumab | NRP1 | |
| Visilizumab | CD3 | Crohn's disease, ulcerative colitis |
| Volociximab | integrin $\alpha_5\beta_1$ | solid tumors |
| Vorsetuzumab mafodotin | CD70 | cancer |
| Votumumab | tumor antigen CTAA16.88 | colorectal tumors |
| Zalutumumab | EGFR | squamous cell carcinoma of the head and neck |
| Zanolimumab | CD4 | rheumatoid arthritis, psoriasis, T-cell lymphoma |
| Zatuximab | HER1 | cancer |
| Ziralimumab | CD147 (basigin) | |
| Zolimomab aritox | CD5 | |

According to a particular embodiment, the anti-cancer agent is an antibody that targets a matrix metalloproteinase. Methods of generating such antibodies are disclosed in U.S. Pat. No. 8,697,078, International Patent Application WO2004/087042 and WO2008/102359, the contents of each are incorporated herein by reference. According to a particular embodiment, the matrix metalloproteinase is Matrix metalloproteinase 9 (MMP-9).

When the anti-LOXL-2 agent is an antibody and the additional anti-cancer agent is an antibody, the present invention further contemplates combining the two antibodies to produce a bispecific antibody.

As used herein, the term "bispecific antibody" refers to an antibody which comprises two antigen binding sites, each binding to a different epitope of a different antigen. The bispecific antibodies of this aspect of the present invention do not share common light chains or common heavy chains.

Bispecific antibodies can be produced by many methods known in the art including for example chemical cross-linkage, genetic engineering, or somatic hybridization, as further described herein below.

Methods of generating bispecific antibodies are disclosed in U.S. Pat. No. 8,268,314, U.S. Patent Application No. 20140017244 and WO 2012/123949, the entire contents of which are incorporated herein by reference.

The bispecific antibodies according to the invention may be "bivalent"—denoting the presence of two binding sites.

According to another embodiment, the antibodies of this aspect of the present invention are trivalent or tetravalent.

The agents of the present invention (or combination of agents) may be tested in vitro for a therapeutic effect. Thus, for example, the agents of the present invention can be tested for their ability to prevent or retard metastasis of tumor cells.

Testing a metastatic phenotype of transformed tumor cells can be performed in vitro since nearly all steps of the metastatic process, including attachment, matrix degradation and migration, can be modeled experimentally in vitro by measuring invasion of a reconstituted basement membrane (RBM). Metastatic invasiveness of tumor cell can be modeled by migration of tumor cells into reconstituted basement membrane (RBM) in the presence and absence of a chemoattractant, such as fibroblast conditioned medium (FCM). The assay determines cells that have attached to the RBM, degraded the RBM enzyinatically and, finally, cells that have penetrated the FCM side of the membrane.

Since in vitro metastasis events correspond to steps observed in the metastatic spread of tumor cells through the basement membrane in vivo, in vitro invasiveness of cells can be assayed by the methods described in Albini et al., 1987 Cancer Research 47: 3239-3245, which is incorporated herein by reference in its entirety. Invasiveness assays and other methods for assessing metastatic affects, are described in Leyton et al., 1994 Cancer Research 54: 3696-3699, which is incorporated by reference herein in its entirety. Reconstituted basement membrane preparations for use in accordance with the hereinabove described assays are readily available from numerous commercial suppliers. One suitable example membrane in this regard is "MATRIGEL" available from Collaborative Biomedical Products of Bedford, Mass.

In vitro evaluation of tumor cell metastatic phenotype can also be effected by determining level and pattern of expression of one or more metastasis associated markers such protease markers, which are considered to be an integral part of tumor metastasis (see U.S. Pat. No. 6,303,318). One example is the arachidonic acid, the release of which in cells can serve to indicate metastatic potential of a tumor (U.S. Pat. No. 6,316,416). In this regard, determining phospholipase A-2 (PLA$_2$) activity, and the activity or abundance of factors that affect the activity of PLA$_2$, such as uteroglobin protein (U.S. Pat. No. 6,316,416) can serve as an indication of metastatic potential.

According to another embodiment, the additional agent is an antifibrotic agent.

The term "antifibrotic agent" refers to one or more chemical or biological compounds that have antifibrotic activity in mammals. These compounds may have different mechanisms of action, some reducing the formation of collagen or another protein, and others enhancing the metabolism or removal of collagen in the affected area of the body. All such compounds having activity in the reduction of the presence of fibrous tissue are included herein, without regard to the particular mechanism of action by which each such drug functions.

An antifibrotic agent, includes, but is not limited to, an agent that degrades or causes the dissolution or shrinkage of fibrotic tissue or a portion thereof, such as for example, the fibrotic tissue in or surrounding the tendon sheaths that pass through the carpal tunnel. In some embodiments, the antifibrotic agent will stretch or relax fibrous tissue (e.g., normal or abnormal fibrous tissue). Abnormal fibrous tissue includes tissue that has an excessive amount or abnormal amount of fibrosis tissue. Normal fibrous tissue includes tissue that has a normal amount of fibrous tissue that is not pathological or indicative of disease. For example, in carpal tunnel syndrome, in some embodiments, the flexor retinaculum generally has normal amounts of fibrous tissue. However, it is beneficial to degrade this normal fibrous tissue so the flexor retinaculum can stretch more easily to accommodate the excess tissue within the carpal tunnel. In some embodiments, the antifibrotic agent can degrade, stretch, and/or relax the normal fibrous tissue, which can be beneficial in treatment of conditions such as scoliosis, tarsal tunnel syndrome, carpal tunnel syndrome and other conditions, where degrading, stretching and/or relaxing healthy or normal fibrosis tissue would be beneficial.

In some embodiments, the antifibrotic agent will enzymatically degrade or shrink the fibrotic tissue. For example, in some embodiments when the antifibrotic agent is an enzyme, it will reduce pressure by degrading proteoglycans (PG) so that PGs are not available to hold water. In some embodiments, the antifibrotic agent can be a protease or glycanase, which is not proteolytic. In some embodiments, the antifibrotic agent, instead of an enzyme, can be an agent that dehydrates the fibrotic tissue, such as for example, a polycationic polymer. In some embodiments, the anti-fibrotic agent may be a hormone, such as for example, relaxin, which inhibits collagen production and stimulates collagen degradation. In some embodiments, the anti-fibrotic agent may be a cytokine, drug, cell, or nucleic-acid-based material that influences the function, viability, or proliferation of fibroblasts or other cells in the fibrotic tissue. In some embodiments, the antifibrotic agent may be cells that inhibit collagen production and/or stimulates collagen degradation.

Antifibrotic agents include, one or more of pancreatic elastase, elastase-2a, elastase-2b, neutrophil elastase, proteinase-3, endogenous vascular elastase, cathepsin G, mast cell chymase, mast cell tryptase, plasmin, thrombin, granzyme B, cathepsin S, cathepsin K, cathepsin L, cathepsin B, cathespin C, cathepsin H, cathespin F, cathepsin G, cathepsin O, cathepsin R, cathepsin V (cathepsin 12), cathepsin W, calpin 1, calpin 2, chondroitinase ABC, chondroitinase AC, hyaluronidase, chymopapain, chymotrypsin, legumain, cathepsin Z (cathepsin X), cathepsin D, cathepsin E, collagenase, matrix metalloproteinases, such as for example, MMP-1 (collagenase-1), MMP-9, MMP-7 (matrilysin), MMP-8 (collagenase-2), MMP-13 (collagenase-3), MMP-18 (collagenase-4), MMP-2 (gelatinase a), MMP-9 (gelatinase b), MMP-3 (stromelysin-1), MMP-10 (stromelysin-2), MMP-11 (stromelysin-3), MMP-7 (matrilysin), MMP-26 (matrilysin), MMP-12 (metalloelastase), MMP-14 (MT1-MMP), MMP-15 (MT2-MMP), MMP-16 (MT3-MMP), MMP-17 (MT4-MMP), MMP-24 (MT5-MMP) transmembrane, MMP-25 (MT6-MMP), gpl anchor, MMP-19, MMP-20 (enamelysin), MMP-x, MMP-23, MMP-27, MMP-28 (epilysin), ADAMTS-1, ADAMTS-2, ADAMTS-3, ADAMTS-4 (aggrecanase-1), ADAMTS-5 (aggrecanase-2), ADAMTS-14, papain, subtilisin, subtilisin A, heparanase. tyrosine kinase inhibitors: imatinib mesylate, dasantinib, nilotinib, inhibitors of PKC-delta and other kinases, TGF-beta receptor inhibitors, HMG-CoA inhibitors, angiotensin inhibitors: angiotensin-converting enzyme inhibitors, angiotensin-II receptor antagonist, pirfenidone, rosiglitazone, cannabinoid receptor, trabedersen, lerdelimumab, metelimumab, mycophenolate mofetil, interferon, or a combination thereof. In some embodiments, the antifibrotic factors include, but are not limited to, interleukins, interferons, cytokines, chemokines, chemotactic molecules, macrophages, lymphocytes, tumor necrosis factor alpha (TNF-alpha), T cells, interferon gamma (IFN-gamma), relaxin, hormones (e.g., progesterone, estrogen, testosterone, growth hormone, thyroid hormone, parathyroid hormone, etc.) or a combination thereof.

The agents of the present invention may be used in diagnostic and therapeutic applications and as such may be included in therapeutic or diagnostic kits.

Thus, compositions of the present invention may, if desired, be presented in a pack or dispenser device, such as an FDA approved kit, which may contain one or more unit dosage forms containing the active ingredient e.g., antibody. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As mentioned, the agents of the present invention are useful for treating diseases associated with aberrant collagen deposition.

Examples of diseases associated with aberrant collagen deposition include cancer (e.g. metastasized cancer), tumor fibrosis, fibrotic diseases.

The term "fibrosis" refers to the formation of fibrous tissue or "fibrotic tissue", usually as a reparative or a reactive process. As used herein, "fibrosis" or "fibroproliferative disease" includes those disorders or disease states that are caused by or accompanied by the abnormal deposition of scar tissue, or by excessive accumulation of collagenous connective tissue. In other embodiments, "fibrosis" includes formation of fibrous tissue that may be a normal part of an organ or tissue. Thus, the antifibrotic agent may be administered to normal or healthy fibrous tissue to provide benefit to the patient (e.g., stretching, relaxing tissue to reduce or prevent pain and/or inflammation). Fibrosis may occur in any organ including, for example, kidney, lung, liver, skin, central nervous system, bone, bone marrow, cardiovascular system, an endocrine organ or the gastrointestinal system. By "fibrosis-associated condition" is meant any condition that is related to fibrosis. Thus, fibrosis-associated conditions may be caused by, be concomitant with, or cause fibrosis.

Examples of pathologic and excessive fibrotic accumulations include, but are not limited to, pulmonary fibrosis, asthma, adult respiratory distress syndrome (ARDS), chronic obstructive pulmonary disease (COPD), idiopathic pulmonary fibrosis (IPF), acute lung injury (ALI), pulmonary fibrosis due to infectious or toxic agents, such as radiation therapy or chemotherapy, pulmonary fibrosis due to particle inhalation, post-transplant pulmonary fibrosis, perirenal fascitis, glomerulonephritis (GN), diabetic nephropathy, renal interstitial fibrosis, renal fibrosis resulting from complications of drug exposure, HIV-associated nephropathy, transplant necropathy, retroperitoneal fibrosis, perivascular fibrosis in Systemic Lupus Erythematosus (SLE), obstruction-induced fibrosis in kidneys or spleen, benign prostate hypertrophy, fibrocystic breast disease, uterine fibroids, ovarian cysts, endometriosis, coronary infarcts, myocardial fibrosis, cerebral infarcts, congestive heart failure, dilated cardiomyopathy, myocarditis, myelofibrosis, vascular stenosis, progressive systemic sclerosis, polymyositis, scleroderma (which affects the skin and the lungs), dermatomyositis, Raynaud's syndrome, retroperitoneal fibrosis, progressive massive fibrosis, nephrogenic systemic fibrosis, Crohn's disease, stenosing tenosynovitis (trigger finger), Dupuytren's disease (palmar fibromatosis), Ledderhose's disease (plantar fibromatosis), Peyronie's disease, fibromatosis colli, keloids, mediastinal fibrosis, rheumatoid arthritis, musculoskeletal fibrosis, post-surgical adhesions, liver fibrosis, autoimmune hepatitis, cirrhosis including primary biliary cirrhosis, viral hepatitis including HIV- or Hepatitis C-induced hepatitis, real fibrotic disease, fibrotic vascular disease, e.g., atherosclerosis, varix, or varicose veins, scleroderma, Alzheimer's disease, diabetic retinopathy, glaucoma, proliferative vitreoretinopathy, fibrosis associated with ocular surgery, chronic transplant rejection, graft vs. host disease, radiation-induced fibrosis, and excessive or hypertrophic scar and/or keloid formation in the dermis occurring during wound healing resulting from trauma or surgical wounds.

Fibrosis also includes healthy or normal production of fibrous tissue. In some embodiments, the antifibrotic agent will stretch or relax fibrous tissue (e.g., healthy or normal fibrous tissue, such as muscles, cartilage, tendons, ligaments, etc.) anywhere in the body. For example, in carpal tunnel syndrome, in some embodiments, the flexor retinaculum generally has normal amounts of fibrous tissue. However, it is beneficial to degrade this normal fibrous tissue so the flexor retinaculum can stretch more easily to accommodate the excess tissue within the carpal tunnel. In some embodiments, the antifibrotic agent can degrade, stretch, and/or relax the normal fibrous tissue, which can be beneficial in treatment of conditions such as scoliosis, tarsal tunnel syndrome, carpal tunnel syndrome and other conditions, where degrading, stretching and/or relaxing healthy or normal fibrous tissue would be beneficial.

In one embodiment, the disorder to be treated is a disorder that results in fibrosis or sclerosis, including but not limited to groups of disorders selected from skeletal muscle fibrosis, irradiation-induced fibrosis, autoimmune-related fibrosis, cardiovascular fibrosis, arteriosclerotic disorders, pulmonary fibrosis, adult respiratory distress syndrome, inflammatory disorders, scleroderma, cirrhosis, keloids, adhesions, hypertrophic scars; skeletal muscle fibrosis associated with a condition, such as muscular dystrophy, denervation atrophy induced by neuromuscular disease, or traumatic injury-induced denervation atrophy; cardiovascular fibrosis selected from left ventricular hypertrophy secondary to hypertension, fibrosis associated with myocardial infarction, fibrosis associated with ischemiareperfusion injury, or fibrosis associated with myocarditis; dermal fibrosis, keloid formation, hypertrophic scar formation, or adhesion formation; pulmonary fibrosis, pulmonary fibrosis due to adult respiratory distress syndrome and irradiation induced fibrosis, or a combination thereof.

In some embodiments, the fibrosis is a localized type of fibrosis, such as for example, stenosing tenosynovitis (trigger finger), Dupuytren's disease (palmar fibromatosis), Ledderhose's disease (plantar fibromatosis), Peyronie's disease, fibromatosis colli, keloids, mediastinal fibrosis, carpal tunnel syndrome, tarsal tunnel syndrome or a combination thereof. Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lymphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to a particular embodiment, the cancer is colorectal cancer, lung cancer, breast cancer (e.g. triple negative breast cancer), renal cancer, ovarian cancer, gastric cancer, bladder cancer, liver cancer, ovarian cancer, fallopian cancer, glioblastoma, leukemia, including acute myeloid leukemia and lymphoma.

According to a particular embodiment, the cancer is a solid tumor.

Treatment of diseases may be effected by administering the agents per se, or together with a carrier as a pharmaceutical composition.

According to one embodiment, the anti-cancer agent or anti-fibrotic agent and the anti-LOXL-2 agent are formulated together in a single composition (e.g. pharmaceutical composition).

According to another embodiment, the anti-cancer agent (or anti-fibrotic agent) and the anti-LOXL-2 agent are formulated in two separate compositions (e.g. two individual pharmaceutical agents).

When administered as separate compositions, the present invention contemplates administering the anti-LOXL-2 prior to administration of the anti-cancer agent (or anti-fibrotic agent), concomitant with administration of the anti-cancer agent (or anti-fibrotic agent) or following administration of the anti-cancer agent (or anti-fibrotic agent).

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent.

Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The present invention also contemplates ex vivo cell therapy using the antibodies described herein, whereby cells and/or tissues are genetically modified to express and secrete the antibodies. Following genetic modification, the cells are then introduced back into the body. The cells may be derived from the patient himself or may be obtained from a donor. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions.

In addition, prolonged absorption of the injectable pharmaceutical form may be brought about by the inclusion of agents which delay absorption such as aluminum monostearate and gelatin.

Regardless of the route of administration selected, the agents of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical art.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

Other contemplated uses of the antibodies of the present invention include purification of analytes; in immunohistochemistry and enzyme immunoassays; for radioimaging and radioimmunotherapy and for drug delivery.

Other contemplated uses are set forth in Cao Y, Suresh M R. Bispecific antibodies as novel bioconjugates. Bioconjug Chem. 1998 November-December; 9(6):635-44, incorporated herein by reference.

It is expected that during the life of a patent maturing from this application many relevant anti-cancer and antifibrotic agents will be developed and the scope of these terms is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Cell Lines and Culture:

The human dermal fibroblast cells were cultured in high-glucose DMEM (Invitrogen) supplemented with 10% (vol/vol) heat-inactivated fetal bovine serum (FBS, Invitrogen), and 100 U/ml penicillin and 100 g/ml streptomycin. Medium was exchanged every 2-3 days and passaged after reaching 80-90% confluence with 0.05% trypsin EDTA (Biological industries). All cell lines were maintained at 37° C. in a humidified atmosphere containing 5% $CO_2$. Fibroblasts were grown on glass coverslips in 24-well dishes until reaching contact inhibition. Then, the medium was replaced with same medium containing 5 ng/ml EGF, 5 μg/ml insulin and 150 μg/ml L-ascorbic acid phosphate magnesium salt n-hydrate to induce ECM secretion, in the presence of PBS or A341 (100 ng/ul). Medium was exchanged every 3 days.

LOXL2 Expression and Purification:

The catalytic domain of human LOXL2 (545-775) was cloned into the pET28 expression vector. The expression vector was transformed into competent *Escherichia coli* BL21, and colonies were selected for kanamycin resistance. Bacteria were grown in LB medium containing 100 μg/ml kanamycin in a shaker flask at 37° C. Protein expression was induced with 0.5 mM IPTG at an OD600=0.6, and cell growth was continued for further 4 hours. Following expression, the enzyme was accumulated in the fraction of inclusion bodies. Cells were harvested by centrifugation and resuspended in a buffer containing 25% sucrose, 50 mM Tris-HCl pH 8, 0.1M NaCl, 0.2 mM EDTA, 1 mM MT, ~10 mg lysozyme and 1 pill of complete protease inhibitor, and stirred for 10~20 min in cold room. The suspension was sonicated (6 cycles, 30-seconds cycles) and centrifuged at 22000 g for 30 min. at 4 C. The pellet was further suspended in buffer containing 2M urea, 2% Triton, 50 mM Tris-HCl pH 8, 0.1M NaCl, 0.2 mM EDTA. 1 mM DTT and centrifuged at 9,000 rpm for 1 hour, sonicated and centrifuged. The pellet was solubilized in 8 M urea, 50 mM MOPS pH 7.5. Then the protein was purified by anion exchange using 6M Urea, 25 mM MOPS pH 7.5 and a gradient of NaCl concentration. The collected protein-containing fractions were diluted <50 ug/1 ml in 6M urea, 25 mM MOPS pH 7.5, 150 mM BME and refolded by using a multi-step dialysis against solution containing 0.4M arginine (non-neutralized), 25 mM MOPS pH 7.5, 200 mM NaCl, 40 uM $CuCl_2$, glutathion reduced, 0.1 mM glutathion oxidized and decreasing concentration of urea (from 2M to 0M). Finally, the enzyme was purified by size exclusion chromatography using a High Load™ 16/60 Superdex™ 75 (Amersham Biosciences) and eluted with 50 mM MOPS pH 7.5, 150 mM NaCl. The eluted fractions were checked for purity on 15% gel by SDS-PAGE, and those containing the LOXL2 protein were pooled and concentrated.

Antibody Generation:

Female BALB/c mice were immunized on day 1 with complete Freund's adjuvant (Disco) and 50 μg of the catalytic domain of LOXL2 and boosted every 2 weeks with incomplete Freund's adjuvant by subcutaneous injection. To generate antibodies, spleens were collected, and B cells were fused with NSO murine myeloma cells 34. Hybridomas were screened with ELISA for immunoreactivity against the catalytic domain of LOXL2 (as described below). Selected hybridomas positive for LOXL2 were subcloned twice and then expanded in tissue culture.

Antibody Purification:

Hybridoma cells of GS341 were grown in DCCM. Cells were collected by centrifugation at 1200 rpm and the supernatant was collected. Supernatant was dialyzed against 20 mM phosphate buffer pH 8. 5 ml HiTrap Protein A HP column was equilibrated with 100 mM phosphate buffer pH 8 and the supernatant was loaded at 5 ml/min. Antibody was eluted with 100 mM citrate buffer pH 6 and dialyzed against PBS or TBS buffers.

Antibody Digestion with Papain:

Papain was activated in 0.5M Tris-HCl pH 8, 10 mM EDTA and 5 mM DTT for 15 mins at 37° C. Active papain was added to a solution of intact ab341 at a ratio of 1:1000, the digestion process was carried for 3 hrs at 37° C. Digestion reaction was terminated with the addition of 20 mM iodoacetamide in the dark at room temperature for 30 mins. The fab fragment was isolated from the Fc by Protein A column, the fab fragment was collected from the flow through and dialyzed against PBS. The purity of the Fab fragment was estimated by 12% SDS-PAGE gel.

Antibody Sequencing:

Total RNA was extracted from the hybridoma cells and cDNA was prepared using SuperScript kit (Invitrogen) as recommended by the manufacturer. The cDNA was used as a template for the PCR reaction using Reddy mix (Termo). For VH and VL amplification the primer mix was used according to Zhou et al. (Zhou et al., 1994). PCR products were purified by gel extraction and used for direct T-A cloning into the pGEM-T plasmid. Ligation products were transformed into DH5α bacteria and grown on LB plates supplemented with Ampicilin, X-gal and IPTG. Positive clones were sent for sequencing, and sequences were analyzed using IMGT-V-QUEST tool.

LOXL1 ELISA Binding Assay:

A 96 well plate (Nunc) was coated with LOXL2 or BSA at 5 µg/ml. After the plate was coated, it was incubated with the antibody for 1 h at 25° C. The bound antibody was detected by peroxidase-conjugated antibody goat anti mouse according to standard procedures. The $EC_{50}$ was calculated from a four-parametric sigmoidal-curve fitting analysis.

Microscale Thermophoresis:

LOXL2 was labeled with 100 nM Alexa647-labeled and incubated with increasing concentration of antibody from 0.1 to 1000 µM in binding buffer containing 50 mM Tris pH 8, 150 mM NaCl, 10 mM $MgCl_2$, 1% BSA and 0.05% Tween. After 15 min incubation, samples were measured using a Monolith NT.115 (Nanotemper, Germany) with 50% Laser-power, Laser on time 35 s, and 40% LED-power.

MST Competition Assay:

Labeled LOXL2 was preincubated with 100 nM bAPN at room temperature for 15 min. Next, the LOXL2:bAPN samples were incubated with increasing concentration of antibody from 0.1 to 1000 µM in binding buffer. After 15 min incubation samples were measured at using a Monolith NT.115 (Nanotemper, Germany) with 50% Laser-power, Laser on time 35 s, and 40% LED-power.

Enzyme Inhibition Assay:

The enzymatic activity of LOXL2 was measured by coupling horse radish peroxidase (HRP) activity to LOXL2 and using the conversion of Amplex Red (Invitrogen) to resofurin as the readout, as described previously, expect collagen type I was used as a substrate (Barry Hamilton et al., Nat Med 16, 1009-17 (2010)). Briefly, collagen type I from rat tail (AdvanceBioMatrix) was naturalized by addition of PBS and NaOH according to manufacture procedure. Prior to the enzymatic assay, LOXL2 was incubated with increasing concentration of antibody for 1 hour in room temperature. The enzymatic reaction was started by adding substrate mixture (50 mM sodium borate, pH 8.0, 100 µM Amplex Red reagent, 0.25 mg/ml Collagen) to the enzyme mixture (50 mM sodium borate, pH 8.0, 2 U/mL HRP, 25 nM LOXL2), and fluorescence was measured using SynergyHT plate reader in kinetics mode with the excitation wavelength at 540 nm and the emission wavelength set to 590 nm. Measurements were made at 30 second intervals for 1 hour at 37° C. As a background, measurements of solution mixture without LOXL2 were conducted, and the signal obtained was subtracted from kinetic measurements. The $IC_{50}$ (the concentration of inhibitor that results in a 50% decrease in activity relative to no inhibitor) was determined by dividing the reaction initial velocities at different antibody concentration with the activity at zero concentration, and fitting the data to the following equation:

ECM Isolation from Tissue Culture:

ECM from individual cultures was decellularized by incubating the cells with 0.5% triton and 20 mM EDTA for 3 days in room temperature, followed by gentle washing with PBS.

Two Photon Microscopy and Second Harmonics Generation:

Samples were imaged using a two-photon microscope in the in-vivo imaging (2 PM:Zeiss LSM 510 META NLO; equipped with a broadband Mai Tai-HP-femtosecond single box tunable Ti-sapphire oscillator, with automated broadband wavelength tuning 700-1020 nm from Spectraphysics, for two-photon excitation). For collagen second harmonic imaging a wavelength of 800 nm was used (detection at 400 nm), using the ×20 objective.

Raman Microscopy:

Raman spectra were acquired using a WITec (Ulm, Germany) Alpha300 R/A/S confocal Raman microscope as described previously[19,20] using excitation wavelength of 532 nm. Imaging was performed by scanning of the laser beam over the sample using an image size is in the range of 150 µm×150 µm, with 300 points per line, and integration time of 0.5 sec. Data analysis was performed using the WITec Project Plus software. Raman images were constructed by integrating the raw data over the vibrational bands of interest. Integration over selected spectral regions was performed by summing up the CCD counts between two frequencies. For example, the C—H stretching band between 2850 cm-1 and 3000 cm-1 was used to image collagen morphology.

Scanning Electron Microscopy:

The ECM was washed with PBS and fixated in 4% paraformaldehyde in PBS for 20 min, followed by 3 washes in PBS. The samples were further incubated with SST for 40 minutes in room temperature followed by 3 washes in water. Ethanol dehydration of samples was then carried out by consecutive washing in increasing concentrations of ethanol (from 30% to 100%), followed by ethanol exchange with liquid $CO_2$ and critical point drying. Finally, samples were coated with a thin layer of gold and imaged in an Ultra microscope (Zeiss).

Metastasis Tests in Animals:

Female CB-17 SCID mice (Harlan Laboratories, Haslett, Mich.; 5 per group) were implanted in the fat pad with RFP-MDA-MB-231 cells ($1.4 \times 10^6$ cells/mouse). Three weeks later, mice were treated twice a week with PBS or 30 mg/kg GS341 for another four weeks. For lung metastasis, lungs were removed and washed, and images were acquired using a fluorescent binocular. In the second experiment, mice were pretreated for four week with PBS or 30 mg/kg Fab GS341 prior to injection of RFP-MDA-MB-231 cells ($1.4 \times 10^6$ cells/mouse) into the mice tail vein, and mice were continued to be treated with PBS or 30 mg/kg Fab GS341 for another four weeks. Metastasis to the lungs was visualized as stated above. Tumors and lungs tissues were preserved in OCT and frozen in −80° C. until use.

ECM Isolation from Tissue:

Tumors were sectioned to 150 µm sections and washed three times with PBS and water. Then, the sample underwent six cycles of freezing on dry ice and thawing in water followed by replacement of water. Final cells removal was accomplished by treatment with $NH_4OH$ for 20 minutes, followed by three wash with water.

Immunofluorescence Analysis:

Murine tumors were fixed in PFA 4%, embedded in paraffin and sectioned. Tumor sections underwent deparafinization and antigen retrieval according to the primary antibody manufacturer's instructions. Sections were permeabilized with 0.5% Triton X-100 in PBS for 5 minutes and blocked with 5% bovine serum albumin (in PBS containing 0.1% Triton) for 1 hour at room temperature. For immunostaining, the cells were incubated overnight at 40° C. with phosphorylated histone H3 (pH3) antibody (Santa Cruz) which were used to analyze cell proliferation. After three washes with PBS, the cells were stained for 1 hour at room temperature with secondary antibodies (abcam) followed by 10 minutes of DAPI (4,6-diamidino-2-phenylindole dihydrochloride) staining. The cells were viewed under a Nikon eclipse 90i fluorescence microscope. Pictures were taken with a 1310 digital camera (DVC, Austin, Tex.).

Statistical Analyses:

All analyses were performed in triplicate for n=3. Tumor growth measurements used the Exact-sig (2×1-tailed) Mann-Whitney test. Statistical analysis was performed with Microsoft Excel using student t-test. Significance levels were set at $P \leq 0.05$, $P \leq 0.01$, and $P \leq 0.001$. Unless otherwise indicated, all graphical data are reported as ±SE.

Example 1

LOXL2 is Critical for Maturation of Collagen in the ECM

ECM secreted by human dermal fibroblast served as a model system to study ECM buildup by stromal cells. Two photon second harmonic generation (SHG) microscopy, which allows label free imaging of collagen fibers on native tissue and cells was used to follow the process of collagen synthesis and assembly at different time points (FIG. 1A). Only after 5 days, a premature form of collagen fibers was visualized. These were still not organized. At day 7 the assembly of linear collagen fibers was observed, which later matured to the characteristic collagen wavy-like higher organization. The expression levels of enzymes belonging to the LOX/LOXL family as well as representative ECM proteins were monitored along a period of four weeks by real-time PCR (FIGS. 2A-D). Interestingly, a gradual increase in LOX expression levels until day 7 was observed followed by total decrease of LOX expression afterward, while expression of LOXL enzymes, and among them LOXL2, was only elevated at later stages (day 14) (FIG. 1B). Therefore, it can be concluded that crosslinking by LOXL enzymes are required for maturation of collagen fibers in the ECM at later stages of assembly of the ECM while LOX is required at the earlier stages. Thus the overexpression of LOXL2 at later stages of collagen assembly, can serve as a therapeutic window to interfere with ECM synthesis during the progression of a disease.

Example 2

GS341 Inhibits Collagen Type I Crosslinking and Maturation of Collagen Fibers

In order to specifically interfere with LOXL2 catalytic activity at the extracellular matrix, the present inventors generated a recombinant catalytic domain of the enzyme composing of residues 545-775 (FIG. 1C). Antibodies were generated using the hybridoma technique by immunizing mice with the generated catalytic fragment, and screening for monoclonal antibodies clones that bind the catalytic domain of LOXL2. Several purified antibodies from positive clones displayed binding affinities to the catalytic domain of LOXL2 as well as to the full length enzyme at the sub-nano molar range using an ELISA binding assay as well as thermoscale thermophoresis measurements of the binding dissociation constant in solution (FIGS. 3A-C). Next, the present inventors screened for an antibody that has an inhibitory activity on collagen crosslinking by LOXL2 by performing an enzymatic activity assay in the presence of monomeric collagen type I as the substrate.

A decrease in the catalytic activity of the enzyme correlated with increasing concentrations GS341 antibody, with an $IC_{50}$ of 1 µM. GS341 bound both human and mouse LOXL2 and was found to be a specific inhibitor of LOXL2. Since invasion is the first process during metastasis, the present inventors further evaluated the inhibitory activity of GS341 in 3D invasion cell-based assay using human metastatic breast cancer cell line MDA-MB-231, that overexpresses almost only LOXL2. The antibody reduced the ability of the cells to invade into the basement membrane by 70% (FIG. 4A). Thus, targeting the enzymatic activity of LOXL2 at the ECM by GS341 has a beneficial effect on a key biological process associated with cancer metastasis.

In order to evaluate the direct effect of GS341 on ECM formation and composition, the present inventors looked into collagen deposition by human dermal fibroblast cells in the presence or absence of the antibody in their growth medium. SHG analysis of control and antibody treated samples did not detect differences in morphology or amount of collagen during the first week of ECM assembly (FIG. 5A). Only after four weeks of growth, it was observed that the control samples displayed a wave-like fibril organization of collagen, while the collagen fibers in the GS341 treated samples remained linear (FIG. 4B). This observation was also confirmed by Raman microscopy of decellularized ECM samples, demonstrating similar effect on ECM organization upon inhibition of LOXL2 (FIG. 4C). In addition, comparison of the averaged Raman spectra for the control and GS341 treated samples further demonstrated shift in vibration peak associated with collagen indicating changes in the chemical properties of the samples (FIG. 6). Mass spectrometry analysis of ECM derived from the control and GS341 treated cells did not detect statistically significant differences in ECM composition indicating that GS341 affects only ECM morphology (FIG. 4D). These results confirm that the enzymatic activity of LOXL2 is required at later stages of ECM deposition during basement membrane formation, and that inhibition of LOXL2 by GS341 prevents maturation of collagen fibers. High resolution scanning electron microscopy imaging of these samples further demonstrated nanoscale changes in fibril directionality within the collagen fibers of the samples. While collagen fibrils of the control samples were assembled in one dominant direction, the collagen fibrils in the antibody treated sample were dispersed and orientated in many directions (FIGS. 4E and 4F). This indicates that crosslinking of collagen fibrils by LOXL2 is required also for proper alignment in the extracellular space.

Example 3

GS341 Affect Breast Cancer Tumor ECM Morphology Leading to Attenuation of Lung Metastasis Overexpression of LOXL2 is associated with poor clinical prognosis for patients and breast cancer tumor are characterized with increasing ECM stiffening with the progression of tumor malignancy. To determine whether inhibition of collagen maturation by LOXL2 has a therapeutic potential on an ECM associated disease, the present inventors quantified the effect of GS341 on breast cancer metastasis. Specifically, triple negative breast cancer MDA-MB-231 cells implanted into the mammary fat pads of immunocompromised nude mice were used. Previously, genetic knock down of LOXL2 in a similar breast cancer model using MB-MDA-231 cells indicated that LOXL2 in not required for primary tumor growth. Therefore the present inventors started treatment with GS341 three weeks after implantation (30 mg per kg body weight twice weekly). Four weeks later both tumor size (FIG. 7A) and metastases in the lungs (FIG. 7B) were measured. Treatment with GS341 not only led to significant decrease in final tumor volume (P=0.02) but also to a significant reduction in metastasis to the lungs. This effect was similar to that obtained by genetic knock-down of LOXL2, indicating that targeting extracellular LOXL2 by an antibody can solely reduce metastasis. In addition, treatment of GS341 significantly reduced cell proliferation in the primary tumors, as shown by immunostaining analysis for markers of cell cycle activity (FIG. 7C).

In order to link between metastasis reduction and the direct effect of LOXL2 on the ECM, changes in the ECM of the primary tumor associated antibody treatment were quantified. Mass spectrometry analysis of tissue samples from the primary tumor detected changes in ECM composition between control and GS341 treated tumors (FIG. 7D). SHG imaging of representative cryo-sections of control tumors depicted massive and linear collagen fibers orientated in a preferred directionality, characteristic of tumors. In sharp contrast, collagen fibers in the GS341 treated tumors, were highly branched and disorientated (FIGS. 7E and 7F). SEM analysis of decellularized tumor sections further depicts that collagen fibrils in the treated tumors have a difference diameter distribution and are thinner compared with the control tumors (FIGS. 7G and 7H). Thus, inhibition of cross-linking by LOXL2 led to the buildup of a different ECM architecture at the tumor microenvironment. Importantly, this effect on collagen architecture is a mirror-image of that observed in the fibroblast experiment in vitro. Thus, inhibition of collagen crosslinking by LOXL2 has a direct effect on the ECM of the primary tumor, leading to attenuation of metastatic seeding in the lungs. Since tumor cells are thought to migrate along linear collagen fibers during the process of tumor invasion and metastasis, it is proposed that GS341 inhibits metastasis by blocking the formation of tumor collagen "high-ways".

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a disease associated with aberrant collagen deposition in a subject in need thereof, comprising administering to the subject a therapeutically effective amount of an antibody which comprises an antigen recognition region which specifically binds to lysyl-oxidase like protein-2 (LOXL-2) and is capable of down-regulating crosslinking of type I collagen in vitro, and wherein said antigen recognition region of said antibody comprises CDR amino acid sequences as set forth in SEQ ID NOs: 3, 4, 5, 6, 7 and 8, thereby treating the disease.

2. The method of claim 1, further comprising administering to the subject an agent selected from the group consisting of an anti-cancer agent and an antifibrotic agent, thereby treating the disease.

3. The method of claim 1, wherein said disease is selected from the group consisting of cancer, pulmonary alveolar proteinosis (PAP) and a fibrotic disease.

4. The method of claim 3, wherein said cancer is breast cancer or colon cancer.

5. The method of claim 4, wherein said breast cancer is triple negative breast cancer.

6. The method of claim 1, wherein said antibody specifically binds to the catalytic site of said LOXL-2.

7. The method of claim 1, wherein said antibody does not bind to the fourth scavenger receptor-cysteine-rich (SRCR) domain of said LOXL-2.

8. The method of claim 1, wherein the amino acid sequence of the $V_H$ of the antibody is as set forth in SEQ ID NO: 1.

9. The isolated antibody of claim 1, wherein the amino acid sequence of the $V_L$ of the antibody is as set forth in SEQ ID NO: 2.

10. The method of claim 2, wherein said anti-cancer agent is cisplatin or an antibody which binds specifically to Matrix metalloproteinase 9 (MMP-9).

11. A method of treating triple negative breast cancer in a subject in need thereof, comprising administering to the subject a therapeutically effective amount of an antibody which comprises an antigen recognition region which specifically binds to the catalytic site of lysyl-oxidase like protein-2 (LOXL-2), wherein said antigen recognition region of said antibody comprises CDR amino acid sequences as set forth in SEQ ID NOs: 3, 4, 5, 6, 7 and 8, thereby treating the triple negative breast cancer.

* * * * *